United States Patent
Stayshich et al.

(10) Patent No.: US 12,344,617 B2
(45) Date of Patent: *Jul. 1, 2025

(54) INDOLONAPHTHOPYRANS

(71) Applicant: Transitions Optical, Ltd., Tuam (IE)

(72) Inventors: Ryan Stayshich, Pittsburgh, PA (US); Darrin R. Dabideen, Pittsburgh, PA (US); Zachary Smith, Pittsburgh, PA (US); Robert W. Walters, Murrysville, PA (US)

(73) Assignee: Transitions Optical, Ltd., Tuam (IE)

( * ) Notice: Subject to any disclaimer, the term of this patent is extended or adjusted under 35 U.S.C. 154(b) by 1034 days.

This patent is subject to a terminal disclaimer.

(21) Appl. No.: 17/416,058

(22) PCT Filed: Dec. 21, 2018

(86) PCT No.: PCT/EP2018/086587
§ 371 (c)(1),
(2) Date: Jun. 18, 2021

(87) PCT Pub. No.: WO2020/126032
PCT Pub. Date: Jun. 25, 2020

(65) Prior Publication Data
US 2022/0056039 A1    Feb. 24, 2022

(51) Int. Cl.
*C07D 491/052*    (2006.01)
*C09K 9/02*    (2006.01)

(52) U.S. Cl.
CPC .......... *C07D 491/052* (2013.01); *C09K 9/02* (2013.01)

(58) Field of Classification Search
CPC .............................................. C07D 491/052
See application file for complete search history.

(56) References Cited

U.S. PATENT DOCUMENTS

| | | | |
|---|---|---|---|
| 5,645,767 A | 7/1997 | Van Gemert | |
| 6,113,814 A | 9/2000 | Gemert et al. | |
| 6,296,785 B1 | 10/2001 | Nelson et al. | |
| 6,392,043 B1 | 5/2002 | Bourchteine et al. | |
| 6,555,028 B2 | 4/2003 | Walters et al. | |
| 7,262,295 B2 | 8/2007 | Walters et al. | |
| 8,608,988 B2 | 12/2013 | Bowles et al. | |
| 9,028,728 B2 | 5/2015 | Bancroft et al. | |
| 10,307,343 B2 | 6/2019 | Bublewitz et al. | |
| 2011/0216273 A1 | 9/2011 | He et al. | |

FOREIGN PATENT DOCUMENTS

| | | |
|---|---|---|
| EP | 2463280 B1 | 9/2013 |
| JP | 2000229974 A | 8/2000 |
| JP | 2003277381 A | 10/2003 |
| WO | 99023071 A1 | 5/1999 |
| WO | 2016142296 A1 | 9/2016 |
| WO | 2017030545 A1 | 2/2017 |

OTHER PUBLICATIONS

Hansch et al., "A Survey of Hammett Substituent Constants and Resonance and Field Parameters", Chem. Rev., 1991, pp. 165-195, vol. 91.

*Primary Examiner* — Shawquia Jackson
(74) *Attorney, Agent, or Firm* — The Webb Law Firm

(57) ABSTRACT

Provided is a photochromic indolenaphthopyran compound having the skeletal structure of Formula (I): wherein $R^1$ and $R^2$ each independently have a steric bulk A, wherein at least one of $R^1$ or $R^2$ has a steric bulk A of at least 0.6, $R^3$ and $R^4$ each independently have a Hammett σp value, and wherein the indolenaphthopyran compound has a calculated electronic steric factor of at least −3.3.

(I)

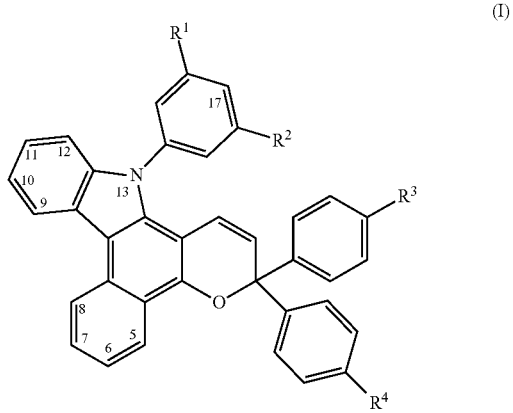

11 Claims, 1 Drawing Sheet

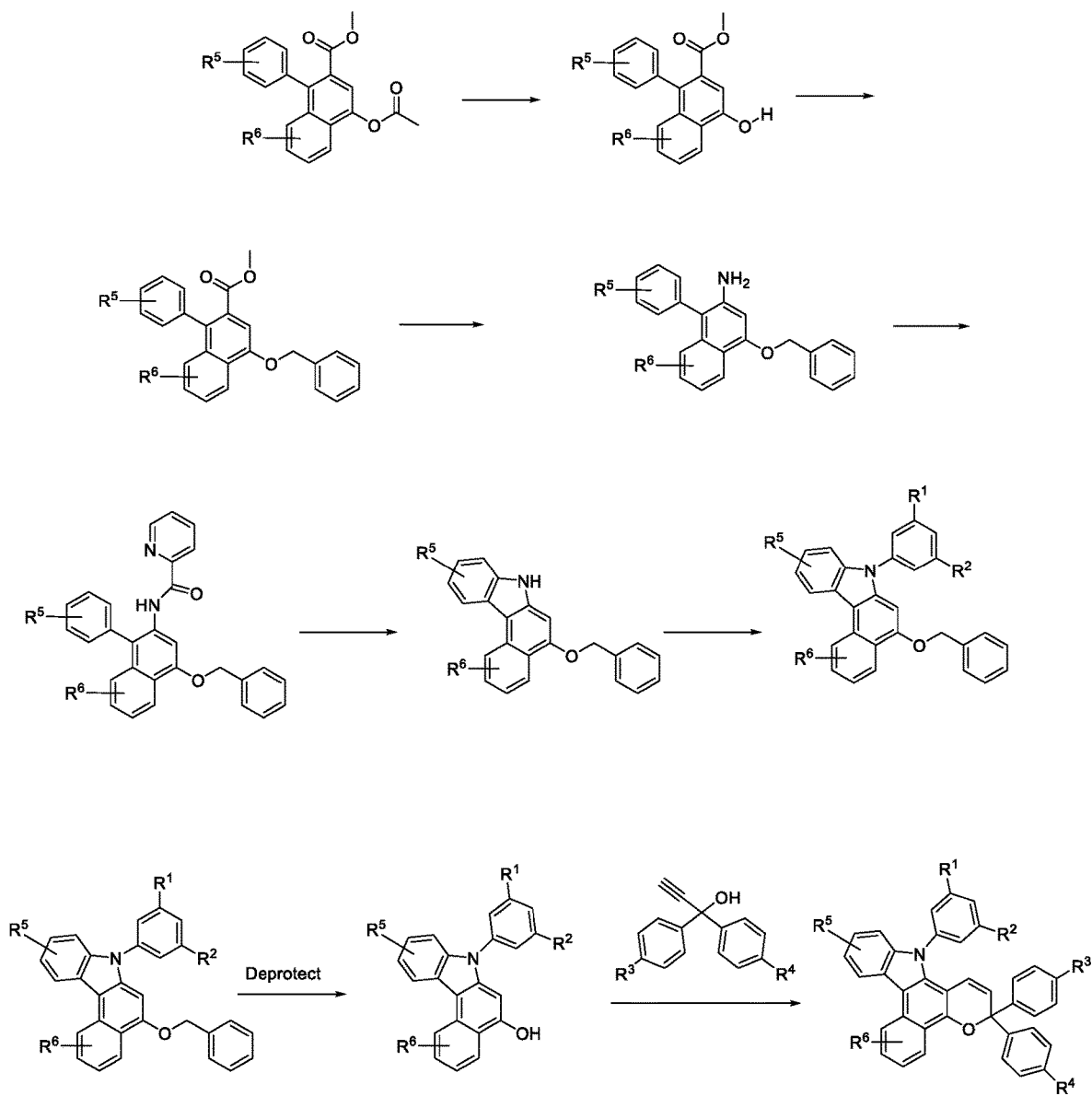

INDOLONAPHTHOPYRANS

CROSS-REFERENCE TO RELATED APPLICATIONS

This application is the U.S. national phase of International Application No. PCT/EP2018/086587 filed Dec. 21, 2018, the disclosure of which is hereby incorporated by reference in its entirety.

FIELD

The present invention relates to photochromic compounds, such as photochromic indolenaphthopyran compounds, and photochromic compositions and photochromic articles that include such photochromic compounds.

BACKGROUND

Photochromic compounds undergo a transformation from one state (or form) to another state in response to certain wavelengths of electromagnetic radiation (e.g., "actinic radiation"). Each state has a characteristic absorption spectrum. For example, many photochromic compounds transform from an unactivated (e.g., bleached or substantially colorless) state to an activated (e.g., tinted) state upon exposure to actinic radiation. When the actinic radiation is removed, the photochromic compounds reversibly transform from the activated state back to the unactivated state.

Photochromic compounds can be characterized with regard to various properties, such as but not limited to: fade rate; change in optical density ($\Delta$OD); the change in optical density ($\Delta$OD) at saturation; sensitivity ($\Delta$OD/Min); the efficiency at which the photochromic compound absorbs radiation required to activate the photochromic compound (chromaticity); bleach color; and dichroic properties such as in the case of photochromic-dichroic compounds, which can be quantified with regard to absorption ratio (AR) values. The change in optical density measures the change from the unactivated state to the activated state.

The indolenaphthopyrans of the present invention provide improved bleach color. For example, placement of an aromatic group on the bridgehead nitrogen significantly improves the bleach color and specific substitutions on said aromatic ring further improves the bleach color compared to naphthopyrans of the prior art. In addition, indolenaphthopyrans generally have more color than their indeno-fused naphthopyrans counterparts in the unactivated state. By selecting specific substituents, the color discrepancy can be improved.

It would be preferred that a photochromic lens would be as clear as a non-photochromic lens of the same material in the unactivated state. Typically non-tinted substrates have a transmission greater than 89% and color a* and b* values less than 1 respectively. Introduction of photochromic compounds onto coatings or into the substrate typically lead to lower transmission and higher color a* and b* values due to residual activation of the chromene. Therefore the residual color of the unactivated state of the photochromic compounds can affect the overall properties of the product and is visible to eye care providers and consumers.

It would be desirable to provide a photochromic compound having enhanced bleach color for improved color and aesthetics. For example, it would be desirable to provide new photochromic indolenaphthopyran compounds with such features.

SUMMARY

A photochromic compound comprises a core skeletal structure represented by the following Formula (I),

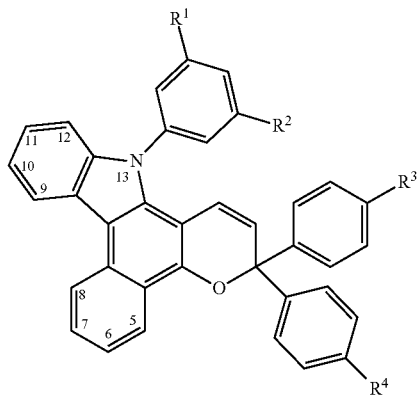

Formula (I)

wherein $R^1$ and $R^2$ each independently have a steric bulk A, and at least one of $R^1$ or $R^2$ has a steric bulk A of at least 0.6; $R^3$ and $R^4$ each independently have a Hammett $\sigma_p$ value; and the compound has a calculated electronic steric factor of at least −3.3.

The features that characterize the present invention are pointed out with particularity in the claims, which are annexed to and form a part of this disclosure. These and other features of the invention, its operating advantages and the specific objects obtained by its use will be more fully understood from the following detailed description in which non-limiting embodiments of the invention are illustrated and described.

BRIEF DESCRIPTION OF THE DRAWING

FIG. 1 illustrates a general scheme, Scheme 1, of an exemplary method for preparing photochromic compounds of the invention.

DETAILED DESCRIPTION

As used herein, the articles "a", "an", and "the" include plural referents unless otherwise expressly and unequivocally limited to one referent.

As used herein, the term "includes" is synonymous with "comprises."

Unless otherwise indicated, all ranges or ratios disclosed herein are to be understood to encompass any and all subranges or subratios subsumed therein. For example, a stated range or ratio of "1 to 10" should be considered to include any and all subranges between (and inclusive of) the minimum value of 1 and the maximum value of 10; that is, all subranges or subratios beginning with a minimum value of 1 or more and ending with a maximum value of 10 or less, such as but not limited to, 1 to 6.1, 3.5 to 7.8, and 5.5 to 10.

As used herein, unless otherwise indicated, left-to-right representations of linking groups, such as divalent linking groups, are inclusive of other appropriate orientations, such as, but not limited to, right-to-left orientations. For purposes of non-limiting illustration, the left-to-right representation of the divalent linking group

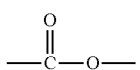

or equivalently —C(O)O—, is inclusive of the right-to-left representation thereof,

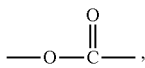

or equivalently —O(O)C— or —OC(O)—.

Other than in the operating examples, or where otherwise indicated, all numbers expressing quantities of ingredients, reaction conditions, and so forth used in the specification and claims are to be understood as modified in all instances by the term "about". By "about" is meant plus or minus twenty-five percent of the stated value, such as plus or minus ten percent of the stated value. However, this should not be considered as limiting to any analysis of the values under the doctrine of equivalents.

As used herein, molecular weight values of polymers, such as weight average molecular weights (Mw) and number average molecular weights (Mn), are determined by gel permeation chromatography using appropriate standards, such as polystyrene standards.

As used herein, the term "polymer" means homopolymers (e.g., prepared from a single monomer species), copolymers (e.g., prepared from at least two monomer species), and graft polymers.

As used herein, the term "(meth)acrylate" and similar terms, such as "(meth)acrylic acid ester" means derivatives of acrylic acid and methacrylic acid, inclusive of acrylate esters, methacrylate esters, acrylamides, methacrylamides, acrylic acid and methacrylic acid. As used herein, the term "(meth)acrylic acid" means methacrylic acid and/or acrylic acid.

The photochromic compounds of the present invention are, with some embodiments, also referred to herein as photochromic-dichroic compounds (such as, when they include one or more mesogen-containing groups, such as IV).

The photochromic compounds of the present invention, as described herein, including, but not limited to, photochromic compounds represented by Formula (I), Formula (Ia), and Formula (Ib), in each case can optionally further include one or more coproducts, resulting from the synthesis of such compounds.

As used herein, the term "photochromic" and similar terms, such as "photochromic compound" means having an absorption spectrum for at least visible radiation that varies in response to absorption of at least actinic radiation. Further, as used herein the term "photochromic material" means any substance that is adapted to display photochromic properties (such as, adapted to have an absorption spectrum for at least visible radiation that varies in response to absorption of at least actinic radiation) and which includes at least one photochromic compound.

As used herein, the term "actinic radiation" means electromagnetic radiation that is capable of causing a response in a material, such as, but not limited to, transforming a photochromic material from one form or state to another as will be discussed in further detail herein.

As used herein, the term "dichroic" means capable of absorbing one of two orthogonal plane polarized components of at least transmitted radiation more strongly than the other.

As used herein, the term "photochromic-dichroic" and similar terms, such as "photochromic-dichroic compound", means possessing and/or providing both photochromic properties (i.e., having an absorption spectrum for at least visible radiation that varies in response to at least actinic radiation), and dichroic properties (i.e., capable of absorbing one of two orthogonal plane polarized components of at least transmitted radiation more strongly than the other).

As used herein, and unless stated otherwise or otherwise limited, the term "photochromic material" includes thermally reversible photochromic materials and compounds and non-thermally reversible photochromic materials and compounds. The term "thermally reversible photochromic compounds/materials" as used herein means compounds/materials capable of converting from a first state, for example a "clear state", to a second state, for example a "colored state", in response to actinic radiation, and reverting back to the first state in response to thermal energy. The term "non-thermally reversible photochromic compounds/materials" as used herein means compounds/materials capable of converting from a first state, for example a "clear state", to a second state, for example a "colored state", in response to actinic radiation, and reverting back to the first state in response to actinic radiation of substantially the same wavelength(s) as the absorption(s) of the colored state (e.g., discontinuing exposure to such actinic radiation).

As used herein, to modify the term "state", the terms "first" and "second" are not intended to refer to any particular order or chronology, but instead refer to two different conditions or properties. For purposes of non-limiting illustration, the first state and the second state of a photochromic compound can differ with respect to at least one optical property, such as but not limited to the absorption of visible and/or UV radiation. Thus, according to various non-limiting embodiments disclosed herein, the photochromic compounds of the present invention can have a different absorption spectrum in each of the first and second state. For example, while not limiting herein, a photochromic compound of the present invention can be clear in the first state and colored in the second state. Alternatively, a photochromic compound of the present invention can have a first color in the first state and a second color in the second state.

As used herein, the term "optical" means pertaining to or associated with light and/or vision. For example, according to various non-limiting embodiments disclosed herein, the optical article or element or device can be chosen from ophthalmic articles, elements and devices; display articles, elements and devices; windows; mirrors; or active and passive liquid crystal cell articles, elements and devices.

As used herein, the term "ophthalmic" means pertaining to or associated with the eye and vision. Non-limiting examples of ophthalmic articles or elements include corrective and non-corrective lenses, including single vision or multi-vision lenses, which can be either segmented or non-segmented multi-vision lenses (such as, but not limited to, bifocal lenses, trifocal lenses and progressive lenses), as well as other elements used to correct, protect, or enhance (cosmetically or otherwise) vision, including without limitation, contact lenses, intra-ocular lenses, magnifying lenses, and protective lenses or visors.

As used herein, the term "display" means the visible or machine-readable representation of information in words, numbers, symbols, designs or drawings. Non-limiting examples of display elements include screens, monitors, and security elements, such as security marks.

As used herein, the term "window" means an aperture adapted to permit the transmission of radiation therethrough. Non-limiting examples of windows include automotive and aircraft transparencies, windshields, filters, shutters, and optical switches.

As used herein, the term "mirror" means a surface that specularly reflects a large fraction of incident light.

As used herein, the term "liquid crystal cell" refers to a structure containing a liquid crystal material that is capable of being ordered. A non-limiting example of a liquid crystal cell element is a liquid crystal display.

As used herein, the terms "formed over", "deposited over", "provided over", "applied over", "residing over", or "positioned over" mean formed, deposited, provided, applied, residing, or positioned on but not necessarily in direct (or abutting) contact with the underlying element, or surface of the underlying element. For example, a layer "positioned over" a substrate does not preclude the presence of one or more other layers, coatings, or films of the same or different composition located between the positioned or formed layer and the substrate.

As used herein, recitations relating to ring positions such as, but not limited to, position-x (e.g., position-3 or position-13) means a particular position in the ring structure, such as the core skeletal structure, of a chemical compound, such as the indolenaphthopyran photochromic compounds of the present invention, and which are depicted herein in accordance with some embodiments by numbers within the ring structures of representative chemical formulas such as, but not limited to Formulas (I), (Ia), and/or (Ib).

By "core skeletal structure" is meant a compound comprising at least the skeletal structure depicted in the associated Formula. The core skeletal structure is provided for purposes of identifying numbered ring positions. However, it is to be understood that, unless specifically shown to the contrary, the core skeletal structure(s) can have one or more atoms or one or more groups (not specifically illustrated on the corresponding Formula) bonded to one or more of the numbered ring positions on the core skeletal structure, which can be the same or different from one another.

The photochromic compounds of the present invention are referred to herein with reference to the term "core skeletal structure," which can be represented by one or more formulas, such as but not limited to Formulas (I), (Ia), and/or (Ib).

All documents or portions of documents, such as but not limited to issued patents and patent applications, referred to herein, and unless otherwise indicated, are to be considered to be "incorporated by reference" in their entirety.

"Aryl group" refers to an aromatic cyclic monovalent hydrocarbon radical, and the term "aromatic" refers to a cyclically conjugated hydrocarbon with a stability (due to delocalization) that is significantly greater than that of a hypothetical localized structure. Examples of aryl groups include $C_6$-$C_{14}$ aryl groups, such as, but not limited to, phenyl, naphthyl, phenanthryl, and anthracenyl.

As used herein, recitations of "halo substituted" and related terms (such as, but not limited to, haloalkyl groups, haloalkenyl groups, haloalkynyl groups, haloaryl groups and halo-heteroaryl groups) means a group in which at least one, and up to and including all of the available hydrogen groups thereof is substituted with a halo group. The term "halo-substituted" is inclusive of "perhalo-substituted". As used herein, the term perhalo-substituted group and related terms (such as, but not limited to, perhaloalkyl groups, perhaloalkenyl groups, perhaloalkynyl groups, perhaloaryl groups or perhalo-heteroaryl groups) means a group in which all of the available hydrogen groups thereof are substituted with a halo group. For example, perhalomethyl is —$CX_3$; perhalophenyl is —$C_6X_5$, where X represents one or more halo groups, such as, but not limited to F, Cl or Br.

As used herein, recitations of "linear or branched" groups, such as linear or branched alkyl, are herein understood to include: groups that are linear (or "straight chain"), such as linear $C_1$-$C_{25}$ alkyl groups; and groups that are appropriately branched, such as branched $C_3$-$C_{25}$ alkyl groups.

The term "alkyl" as used herein means linear or branched, cyclic or acyclic $C_1$-$C_{25}$ alkyl. Linear or branched alkyl can include $C_1$-$C_{25}$ alkyl, such as $C_1$-$C_{20}$ alkyl, such as $C_2$-$C_{10}$ alkyl, such as $C_1$-$C_{12}$ alkyl, such as $C_1$-$C_6$ alkyl. Examples of alkyl groups from which the various alkyl groups of the present invention can be selected from, include, but are not limited to, those recited further herein. Alkyl groups can include "cycloalkyl" groups. The term "cycloalkyl" as used herein means groups that are appropriately cyclic, such as, but not limited to, $C_3$-$C_{12}$ cycloalkyl (including, but not limited to, cyclic $C_5$-$C_7$ alkyl, or cyclic $C_3$-$C_{10}$ alkyl) groups. Examples of cycloalkyl groups include, but are not limited to, those recited further herein. The term "cycloalkyl" as used herein also includes: bridged ring polycycloalkyl groups (or bridged ring polycyclic alkyl groups), such as, but not limited to, bicyclo[2.2.1]heptyl (or norbornyl) and bicyclo[2.2.2]octyl; and fused ring polycycloalkyl groups (or fused ring polycyclic alkyl groups), such as, but not limited to, octahydro-1H-indenyl, and decahydronaphthalenyl.

The term "heterocycloalkyl" as used herein means groups that are appropriately cyclic, such as, but not limited to, $C_2$-$C_{12}$ heterocycloalkyl groups, such as $C_5$-$C_7$ heterocycloalkyl groups, such as $C_2$-$C_{10}$ heterocycloalkyl groups, and which have at least one hetero atom in the cyclic ring, such as, but not limited to, O, S, N, P, and combinations thereof. Examples of heterocycloalkyl groups include, but are not limited to, imidazolyl, tetrahydrofuranyl, tetrahydropyranyl and piperidinyl. The term "heterocycloalkyl" as used herein, also includes: bridged ring polycyclic heterocycloalkyl groups, such as, but not limited to, 7-oxabicyclo[2.2.1]heptanyl; and fused ring polycyclic heterocycloalkyl groups, such as, but not limited to, octahydrocyclopenta[b]pyranyl, and octahydro-1H-isochromenyl.

The term "heteroaryl", as used herein, includes, but is not limited to, $C_3$-$C_{18}$ heteroaryl, such as, but not limited to, $C_3$-$C_{10}$ heteroaryl (including fused ring polycyclic heteroaryl groups) and means an aryl group having at least one hetero atom in the aromatic ring, or in at least one aromatic ring in the case of a fused ring polycyclic heteroaryl group. Examples of heteroaryl groups include, but are not limited to, furanyl, pyranyl, pyridinyl, isoquinoline, and pyrimidinyl.

As used herein, the term "fused ring polycyclic-aryl-alkyl group" and similar terms such as fused ring polycyclic-alkyl-aryl group, fused ring polycyclo-aryl-alkyl group, and fused ring polycyclo-alkyl-aryl group means a fused ring polycyclic group that includes at least one aryl ring and at least one cycloalkyl ring that are fused together to form a fused ring structure. For purposes of non-limiting illustration, examples of fused ring polycyclic-aryl-alkyl groups include, but are not limited to indenyl, 9H-flourenyl, cyclopentanaphthenyl, and indacenyl.

The term "aralkyl", as used herein, includes, but is not limited to, $C_6$-$C_{24}$ aralkyl, such as, but not limited to, $C_6$-$C_{10}$ aralkyl, and means an alkyl group substituted with an aryl group. Examples of aralkyl groups include, but are not limited to, benzyl and phenethyl.

Representative alkyl groups include, but are not limited to, methyl, ethyl, propyl, isopropyl, butyl, isobutyl, sec-butyl, tert-butyl, pentyl, neopentyl, hexyl, heptyl, octyl, nonyl and decyl. Representative alkenyl groups include, but are not limited to, vinyl, allyl and propenyl. Representative alkynyl groups include, but are not limited to, ethynyl, 1-propynyl, 2-propynyl, 1-butynyl, and 2-butynyl. Representative cycloalkyl groups include, but are not limited to, cyclopropyl, cyclobutyl, cyclopentyl, cyclohexyl, and cyclooctyl substituents. Representative heterocycloalkyl groups include, but are not limited to, imidazolyl, tetrahydrofuranyl, tetrahydropyranyl and piperidinyl. Representative aryl groups include, but are not limited to, phenyl, naphthyl, anthracynyl, phenanthrenyl, and tetracenyl (including structural isomers thereof). Representative heteroaryl groups include, but are not limited to, furanyl, pyranyl, pyridinyl, isoquinolinyl, and pyrimidinyl. Representative aralkyl groups include, but are not limited to, benzyl and phenethyl.

The term "nitrogen-containing heterocycle", as used herein, includes, but is not limited to, a nitrogen-containing ring wherein the nitrogen-containing ring is bonded through a ring nitrogen. Examples of nitrogen-containing heterocycles include, but are not limited to, cyclic aminos, such as morpholino, piperidino, and pyrrolidino; and heteroaromatics, such as imidazole, pyrrole, indole, and carbazole.

As used herein, recitations of "substituted" group, means a group including, but not limited to, alkyl group, heterocycloalkyl group, aryl group, and/or heteroaryl group, in which at least one hydrogen thereof has been replaced or substituted with a group that is other than hydrogen, such as, but not limited to, alkoxy groups; halo groups (e.g., F, Cl, I, and Br); hydroxyl groups; thiol groups; alkylthio groups; arylthio groups; ketone groups; aldehyde groups; ester groups; carboxylic acid groups; phosphoric acid groups; phosphoric acid ester groups; sulfonic acid groups; sulfonic acid ester groups; nitro groups; cyano groups; alkyl groups (including aralkyl groups); alkenyl groups; alkynyl groups; haloalkyl groups; perhaloalkyl groups; heterocycloalkyl groups; aryl groups (including alkaryl groups, including hydroxyl substituted aryl, such as phenol, and including poly-fused-ring aryl); heteroaryl groups (including poly-fused-ring heteroaryl groups); amino groups, such as —N($R^{11'}$)($R^{12'}$) where $R^{11'}$ and $R^{12'}$ are each independently selected, for example, from hydrogen, alkyl, heterocycloalkyl, aryl, or heteroaryl; carboxylate groups; siloxane groups; alkoxysilane groups; polysiloxane groups; amide groups; carbamate groups; carbonate groups; urea groups; polyester groups; polyether groups; polycarbonate groups; polyurethane groups; acrylate groups; methacrylate groups; nitrogen-containing heterocycles; or combinations thereof, including those classes and examples as described further herein.

As used herein, "at least one of" is synonymous with "one or more of", whether the elements are listed conjunctively or disjunctively. For example, the phrases "at least one of A, B, and C" and "at least one of A, B, or C" each mean any one of A, B, or C, or any combination of any two or more of A, B, or C. For example, A alone; or B alone; or C alone; or A and B; or A and C; or B and C; or all of A, B, and C.

As used herein, "selected from" is synonymous with "chosen from", whether the elements are listed conjunctively or disjunctively. Further, the phrases "selected from A, B, and C" and "selected from A, B, or C" each mean any one of A, B, or C, or any combination of any two or more of A, B, or C. For example, A alone; or B alone; or C alone; or A and B; or A and C; or B and C; or all of A, B, and C.

The discussion of the invention may describe certain features as being "particularly" or "preferably" within certain limitations (e.g., "preferably", "more preferably", or "even more preferably", within certain limitations). It is to be understood that the invention is not limited to these particular or preferred limitations but encompasses the entire scope of the disclosure.

The invention comprises, consists of, or consists essentially of, the following aspects of the invention, in any combination.

The present invention according to Formula I, Formula Ia, and/or Formula Ib combines the steric effect of the functional groups $R^1$ and $R^2$ with the electronic effects of the $R^3$ and $R^4$ groups to give an acceptable color expressed as Delta $E_{\%\ T}$. Delta E % T relates the percent transmission (% T), the a* values, and b* values of the unactivated photochromic layer to that of the transparent substrate (T*$_0$, a*$_0$, b*$_0$) according to Equation 1.

$$\text{Delta } E_{\%\ T} = [(\%\ T - \%\ T_o)^2 + (a^* - a^*_o)^2 + (b^* - b^*_o)^2]^{0.5} \quad \text{Equation 1}$$

The lower the Delta $E_{\%\ T}$ value, the less tint and color the sample possesses, in this case in the unactivated state. The relationship of the steric effects of $R^1$ and $R^2$ with electronic effects of $R^3$ and $R^4$ can be expressed and predicted by the electronic-steric factor (ESF) according to Equation 2.

$$\text{ESF} = [(\text{sum of Hammett } \sigma_p \text{ values for } R^3 \text{ and } R^4)) \times 10] + (\text{sum of steric } A \text{ values for } R^1 \text{ and } R^2) \quad \text{Equation 2}$$

The relative strength of electron donor groups is frequently described by Hammett Sigma values, or $\sigma_p$ values. The more negative the Hammett Sigma value, the more colored the unactivated state can appear. It has been found that steric bulk in specific positions can overcome this undesired coloration. The steric bulk required to overcome the residual unactivated color increases as the electron donating strength increases (i.e., the Hammett Sigma value gets more negative).

As can be seen from Equation 2, the electronic-steric factor (ESF) is calculated from the sum of literature Hammett values for $R^3$ and $R^4$ (multiplied by 10 to generate comparable units) and the sum of the literature steric A values of $R^1$ and $R^2$. A list of Hammett $\sigma_p$ values for various substituents can be found in C. Hansch, A. Leo, and R. W. Taft, "A Survey of Hammett Substituent Constants and Resonance and Field Parameters", Chem. Rev., 1991, 91, 165-195, which disclosure is incorporated herein by reference. Hammett $\sigma_p$ values for selected substituents of the present invention, for example, include those listed in Table 1 below.

TABLE 1

Hammett $\sigma_p$ Values for Selected Substituents

| Substituent | $\sigma_p$ value | Substituent | $\sigma_p$ value |
| --- | --- | --- | --- |
| —H | 0 | —Phenyl | −0.01 |
| —CH$_3$ | −0.17 | —NHCOOEt | −0.15 |
| —OCH$_3$ | −0.27 | —F | 0.062 |
| —N(CH$_3$)$_2$ | −0.84 | —Cl | 0.23 |
| —Morpholino | −0.65 (est) | —SCH$_3$ | 0.0 |
| —OCOMe | 0.31 | —SPh | 0.07 |
| —COOC$_2$H$_5$ | 0.45 | —CN | 0.66 |
| —OH | −0.37 | —CF$_3$ | 0.54 |

A list of steric A values for various substituents can be found in Gordon, Arnold J. Ford, Richard A., "Chemist's Companion—A Handbook of Practical Data, Techniques, and References—3.3 Conformational Free Energy Values", 1972, John Wiley & Sons, 156-157, which disclosure is incorporated herein by reference. Steric A values for selected substituents of the present invention, for example, include those listed in Table 2 below.

TABLE 2

Steric A Values for Selected Substituents

| Substituent | A value (kcal/mol) | Substituent | A Value (kcal/mol) |
|---|---|---|---|
| Hydrogen | 0 | Ethyl | 1.75 |
| Fluorine | 0.15 | Isopropyl | 2.15 |
| Chlorine | 0.43 | Trifluoromethyl | 2.1 |
| Bromine | 0.38 | Cyclohexyl | 2.15 |
| Methoxy | 0.60 | Phenyl | 3 |
| Methyl | 1.70 | t–Butyl | >5 |

Referring to Equation 1, a lower Delta $E_{\%\ T}$ can be achieved by increasing the steric bulk of $R^1$ and $R^2$ or by incorporating less electron donating $R^3$ and $R^4$ groups. In many cases it is desirable to use stronger donating $R^3$ and $R^4$ groups to provide faster fade rates and to alter the absorption spectra of the activated chromene. Increasing the ESF value lowers the Delta $E_{\%\ T}$, and thus improves bleach state color. That is, the greater the ESF value, the better the bleach color of the photochromic compound. When the ESF is greater than −3.3, the Delta $E_{\%\ T}$ becomes acceptable (less than 7) for a photochromic product which employs the photochromic compound. A preferred Delta $E_{\%\ T}$ for a photochromic compound, for example, is less than 3.5, such as less than 3, such as less than 2.5, or such as less than 2.

The photochromic compounds according to the present invention can be represented by one or more of the core skeletal structures described below. Each available numbered ring position (e.g., 5, 6, 7, 8, 9, 10, 11, 12 and/or 17) of the core skeletal structure of Formula (I) can have covalently bonded thereto hydrogen or a group other than hydrogen, for example, such as a group described herein. Examples of such groups are described below.

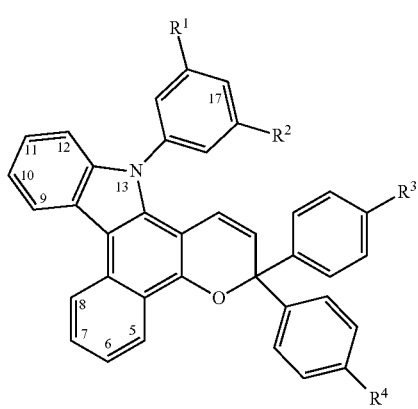

(I)

With reference to Formula (I), $R^1$ and $R^2$ each independently have a steric bulk A, and at least one of $R^1$ or $R^2$ has a steric bulk A of at least 0.6. Examples of groups from which $R^1$ and $R^2$ can be selected include, but are not limited to, alkoxy such as methoxy, ethoxy, and butoxy; linear or branched alkyl such as methyl, ethyl, isopropyl, tert-butyl, and neopentyl; perfluorinated alkyl such as trifluoromethyl and pentafluoroethyl; cycloalkyl such as cyclopentyl and cyclohexyl; and aryl such as phenyl.

$R^3$ and $R^4$ each independently have a Hammett $\sigma_p$ value ranging from of −0.84 to 0.23. Any substituent with a Hammett value within the recited range maybe used provided the combined steric value A of $R^1$ and $R^2$ is sufficient to overcome the combined Hammett values to satisfy the calculated electronic steric factor (ESF) requirement described above.

The indolenaphthopyran compound of Formula (I) has a calculated electronic steric factor of at least −3.3. For example, the indolenaphthopyran compound can have a calculated electronic steric factor of at least 0.

At least one of $R^1$ and $R^2$ can each independently be alkyl, alkoxy, haloalkyl, or a nitrogen-containing heterocycle. For example, at least one of $R^1$ or $R^2$ can be methyl, ethyl, butyl, tert-butyl, trifluoromethyl, or methoxy. Both $R^1$ and $R^2$ can be the same group. At least one of $R^3$ and $R^4$ can each independently be hydrogen, alkyl, alkoxy, haloalkyl, or a nitrogen-containing heterocycle. For example, at least one of $R^3$ or $R^4$ can be methoxy or trifluoromethyl.

Additionally or alternatively, the photochromic compounds of the present invention can be represented by the core skeletal structure of Formula (Ia):

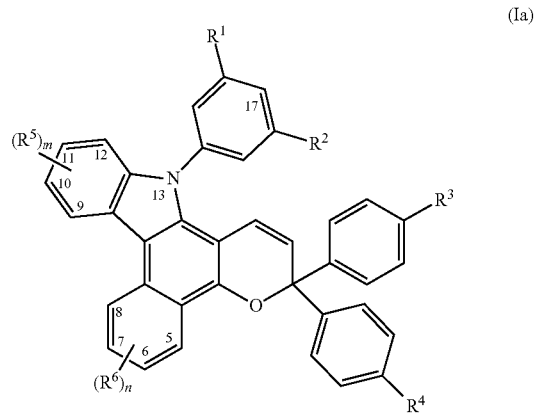

(Ia)

With reference to Formula (Ia), $R^1$, $R^2$, $R^3$, and $R^4$ are as previously described with respect to Formula (I).

With further reference to Formula (Ia), m is 0 to 4, n is 0 to 4, and $R^5$ independently for each m and $R^6$ independently for each n are hydroxyl; cyano; (meth)acrylate; amino or nitrogen-containing heterocycle; a mesogen-containing group L; substituted or unsubstituted alkyl; substituted or unsubstituted alkenyl; substituted or unsubstituted alkynyl; a halo group; a perhalo group; boronic ester or boronic acid; polyether, polyester, polycarbonate, or polyurethane; substituted or unsubstituted aryl; substituted or unsubstituted heterocycloalkyl; substituted or unsubstituted heteroaryl; substituted or unsubstituted alkoxy or substituted or unsubstituted aryloxy; substituted or unsubstituted alkylthio or substituted or unsubstituted arylthio; ketone, aldehyde, ester, carboxylic acid, carboxylate, or amide; carbonate, carbamate, or urea; or siloxane, alkoxysilane, or polysiloxane. Each alkyl substituent, each alkenyl substituent, each alkynyl substituent, each aryl substituent, each heterocycloalkyl substituent, each heteroaryl substituent, each alkoxy substituent, each aryloxy substituent, each alkylthio substituent, and each arylthio substituent is in each case independently selected from halogen, cyano, nitro, alkyl, alkenyl, alkynyl, haloalkyl, perhaloalkyl, heterocycloalkyl, aryl, heteroaryl, alkoxy, hydroxyl, alkylthio, ketone, aldehyde, ester, carboxylic acid, carboxylate, siloxane, alkoxysilane, polysiloxane, amide, amine, carbamate, carbonate, urea, polyester group, polyether group, polycarbonate group, polyurethane group, an acrylate group, a methacrylate group, aryl amine, alkyl amine, cyclic aminos, heteroaromatics, or combinations thereof.

For example, $R^1$ can be trifluoromethyl, $R^2$ can be trifluoromethyl or hydrogen, and $R^3$ and $R^4$ can be hydrogen.

With further reference to Formula (Ia), each mesogen-containing group $L^1$ can independently be represented by the following Formula (II), $$[S^1]_c\text{-}[Q^1\text{-}[S^2]_d]_{d'}\text{-}[Q^2\text{-}[S^3]_e]_{e'}[Q^3[S^4]_f]_{f'}\text{---}R \qquad \text{Formula (II)}$$

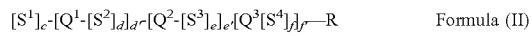

$Q^1$, $Q^2$, and $Q^3$ for each occurrence, are independently a divalent group selected from the group consisting of unsubstituted aryl, substituted aryl, unsubstituted cycloalkyl, and substituted cycloalkyl. The aryl substituents and cycloalkyl substituents can each independently be selected from the group consisting of liquid crystal mesogens, halogen, alkyl, alkoxy, alkylamino, dialkylamino, alkylthio, alkoxycarbonyl, alkylcarbonyl, alkoxycarbonyloxy, aryloxycarbonyloxy, perfluoroalkyl, and perfluoroalkoxy. With further reference to Formula (II), c, d, e, and f are each independently an integer of 0 to 3; and each $S^1$, $S^2$, $S^2$, and $S^4$ is independently chosen for each occurrence from a spacer unit selected from the group consisting of: (i) —C(Z)$_2$—, —N(Z)—, —C(Z)=C(Z)—, —C(Z)=N—, wherein Z for each occurrence is independently selected from the group consisting of hydrogen, alkyl, or aryl; (ii) —Si(CH$_3$)$_2$—, —Si(CH$_3$)$_2$O—; and (iii) —O—, —C(=O)—, —C≡C—, —N=N—, —S—, —S(=O)—, —(O=)S(=O)—, —(O=)S(=O)O—, —O(O=)S(=O)O—, provided that when two spacer units comprising heteroatoms are linked together the spacer units are linked so that heteroatoms are not directly linked to each other. With further reference to Formula (II), R is alkyl. With further reference to Formula (II), d', e' and f' are each independently 0, 1, 2, 3, and 4, provided that the sum of d'+e'+f' is at least 1.

Additionally or alternatively, the photochromic compounds of the present invention can be represented by the core skeletal structure of Formula (Ib):

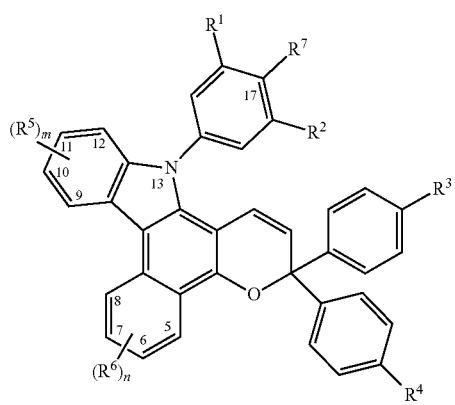

With reference to Formula (Ib), $R^1$, $R^2$, $R^3$, $R^4$ $R^5$, and $R^6$ are as previously described with respect to Formulas (I) and/or (Ia).

With further reference to Formula (Ib), $R^7$ is selected from the group consisting of alkyl, alkoxy, haloalkyl, and a nitrogen-containing heterocycle.

As used herein, the term "polysiloxane" such as with regard to substituents of various groups of the photochromic compounds of the present invention, includes a material represented by the following Formula (G):

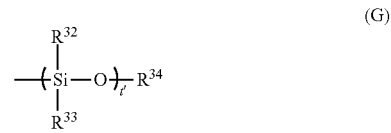

With reference to Formula (G), subscript t' is from 2 to 200, such as from 2 to 100, or 2 to 50, or from 2 to 25, or from 2 to 15, or from 2 to 10, or from 2 to 5, in each case inclusive of the recited values. With further reference to Formula (G): $R^{32}$ and $R^{33}$, for each t', are each independently selected from alkyl or aryl; and $R^{34}$ is selected from hydrogen, alkyl, or aryl. With some embodiments: $R^{32}$ and $R^{33}$ for each t', are each independently selected from methyl, ethyl, or phenyl; and $R^{34}$ is selected from hydrogen, methyl, ethyl, or phenyl.

As used herein, the term "polysiloxane" such as with regard to substituents of various groups of the photochromic compounds of the present invention, alternatively to or in addition to a material represented by Formula (G), includes a material represented by the following Formula (H):

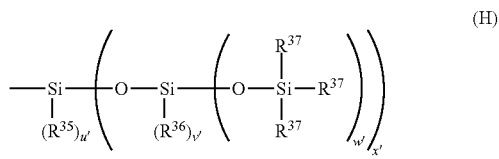

With reference to Formula (H), subscript u' is 0-2 and subscript x' is 1-3, provided that u'+x' is 3; and subscript v' is 0-2 and subscript w' is 1-3, provided that v'+w' is 3. With further reference to Formula (H), $R^{31}$ independently for each u', $R^{36}$ independently for each v' and each x', and each $R^{37}$ independently for each w' and each x', are in each case independently selected from alkyl (such as, but not limited to, methyl or ethyl) or aryl (such as, but not limited to, phenyl).

With some embodiments, the photochromic compounds of the present invention, such as those described with reference to Formulas (I), (Ia) and/or (Ib) can each be used alone, or in combination with one or more other photochromic compounds. For example, the photochromic compounds of the present invention can be used in conjunction with one or more other photochromic compounds having activated absorption maxima within the range of 300 to 1,000 nanometers. Further, the photochromic compounds according to the present invention can be used in conjunction with one or more complementary conventional polymerizable or compatibilized photochromic compounds, such as for example, those disclosed in U.S. Pat. No. 6,113,814 (at col. 2, line 39 to col. 8, line 41), and U.S. Pat. No. 6,555,028 (at col. 2, line 65 to col. 12, line 56).

The photochromic compounds of the present invention can be used in combination with a mixture of other photochromic compounds. For example, although not limiting herein, mixtures of photochromic compounds can be used to attain certain activated colors, such as a near neutral gray or near neutral brown. See, for example, U.S. Pat. No. 5,645, 767, col. 12, line 66 to col. 13, line 19, which describes the parameters that define neutral gray and brown colors.

Examples of classes of other photochromic compounds that can be used in combination with the photochromic compounds of the present invention, include, but are not limited to, indeno-fused naphthopyrans, naphtho[1,2-b]pyrans, naphtho[2,1-b]pyrans, phenanthrenopyrans, quinolinopyrans, fluoroanthenopyrans, spiropyrans, benzoxazines, naphthoxazines, spiro(indoline)naphthoxazines, spiro(indoline)pyridobenzoxazines, spiro(indoline)fluoranthenoxazines, spiro(indoline)quinoxazines, fulgides, fulgimides, diarylethenes, diarylalkylethenes, diarylalkenylethenes, thermally reversible photochromic compounds, and non-thermally reversible photochromic compounds, and mixtures thereof. Further examples of other photochromic compounds that can be used in combination with the photochromic compounds of the present invention include, but are not limited to, those disclosed at column 34, line 20 through column 35, line 13 of U.S. Pat. No. 9,028,728 B2.

The indolenaphthopyran compounds of the present invention can be prepared in accordance with art-recognized methods as follows. For purposes of non-limiting illustration and with reference to FIG. 1, general synthetic Scheme 1, the preparation of photochromic compounds according to the present invention is described as follows. Further detailed descriptions of the preparation of photochromic compounds of the present invention are provided further herein in the Examples. In FIG. 1, the various groups, such as $R^1$, $R^2$, $R^3$, $R^4$, $R^5$, $R^6$, $R_{aryl}$, and $R_{alkyl}$ of the various intermediates, reactants, and/or compounds depicted, are each as described herein, and/or represent precursors of such groups.

The synthesis of compounds depicted below as Formula III has been described in numerous references such as U.S. Pat. No. 6,296,785 or U.S. Pat. No. 7,262,295, with varying substituents.

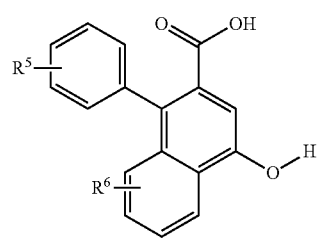

(III)

The hydroxyl group and the carboxylic acid group can be benzylated by reacting with benzyl chloride and a base such as sodium or potassium carbonate. The carboxylic ester that is formed can then be converted to the carboxylic acid by either acid or basic methods for ester hydrolysis. The resulting product is depicted below as Formula IIIa.

(IIIa)

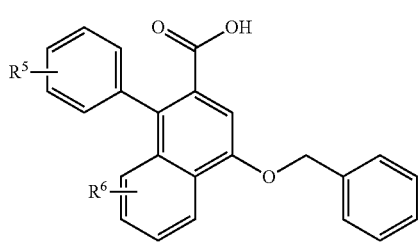

The carboxylic acid group can then be converted to an $NH_2$ group via Curtius rearrangement conditions using diphenyl phosphorylazide which generates the isocyanate group followed by hydrolysis to yield the amine group, as depicted below in Formula IIIb.

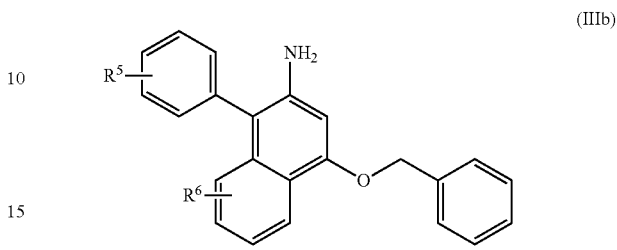

(IIIb)

The amine group is converted to an indole by first forming the picolinamide group by traditional amide forming reactions such as reacting the amine with acid chlorides, esters, or carboxylic acid groups. Reaction of the amine with picolinoyl chloride with a base such as triethylamine gives the picolinamide, as depicted in Formula IIIc, in high yields. The picolinamide can be cyclized to the indole, as depicted in Formula IIId, by use of a copper catalyst as described in Takumatso, K. et al. *Org. Lett.* 2014, 16, 2892. See reaction depicted below.

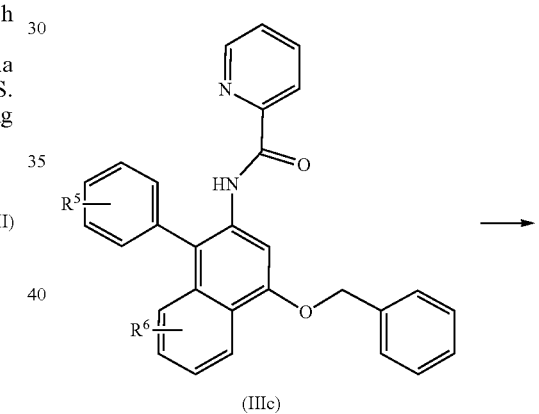

(IIIc)

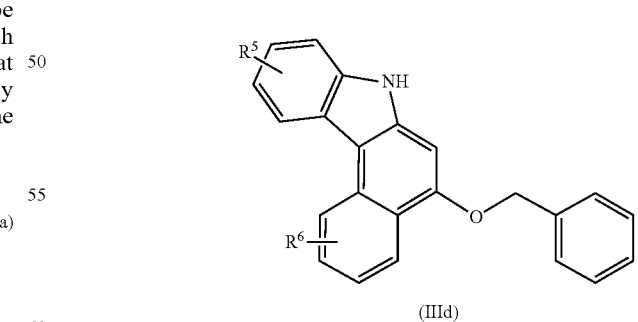

(IIId)

The indole ring as depicted in Formula IIId can also be formed by reacting the amine of Formula IIIb with Tosyl (Ts) chloride or anhydride to form a N-Ts group, as depicted in Formula IIIe. This group can be cyclized with palladium catalyst as described in Youn, S. W. *Org. Lett.* 2011, 13, 3738. See reaction depicted below.

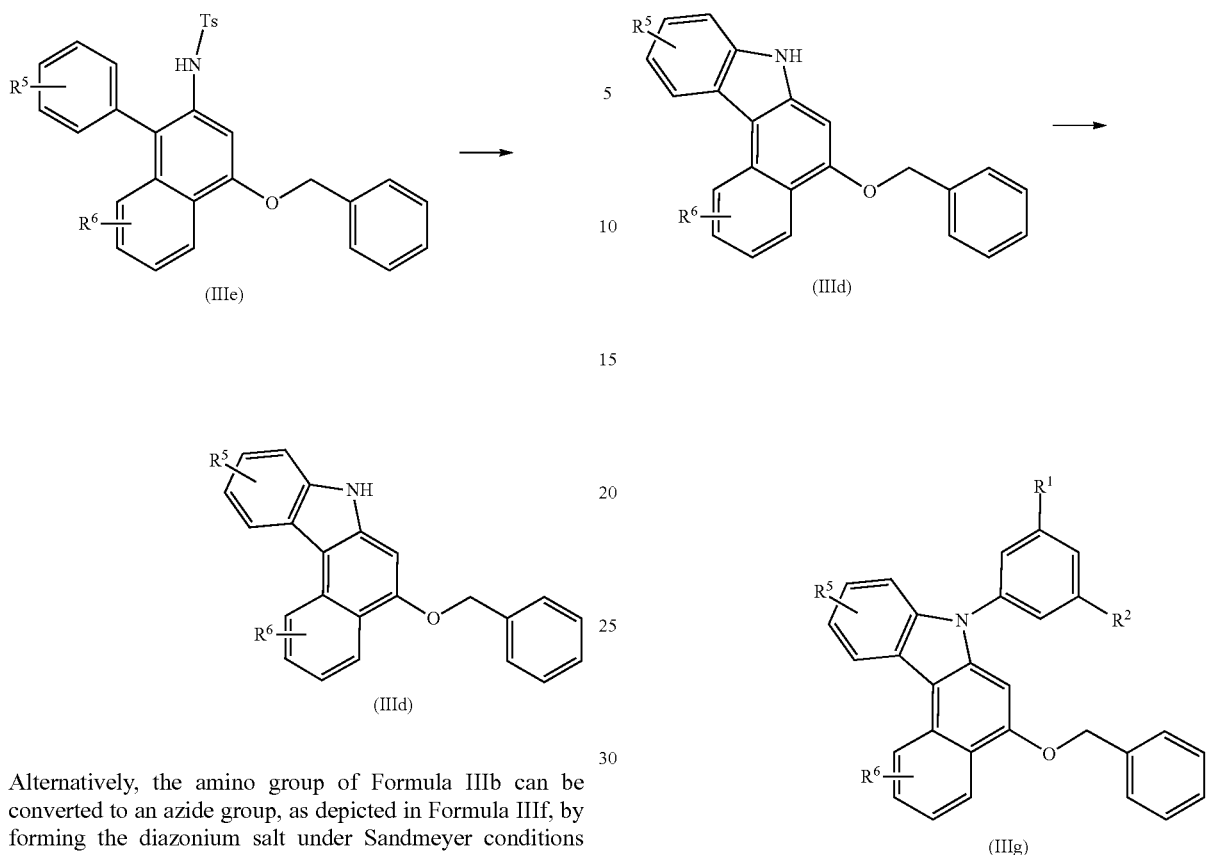

Alternatively, the amino group of Formula IIIb can be converted to an azide group, as depicted in Formula IIIf, by forming the diazonium salt under Sandmeyer conditions followed by displacement with a salt of azide such as sodium azide. The indole group of Formula IIId can then be formed by exposure to UV light in a solvent such as THF. See reaction depicted below.

The indole can also be arylated as depicted in Formula IIIg via nucleophilic aromatic substitution, such as by reaction with an aryl fluoride in a suitable solvent such as tetrahydrofuran or dimethylformamide.

The benzyl protecting group can be removed by palladium hydrogenation conditions or with a strong acid. See reaction depicted below, where Formula IIIg refers to an indole substituted with any R⁴ as described herein, and the deprotected product is shown in Formula IIIh.

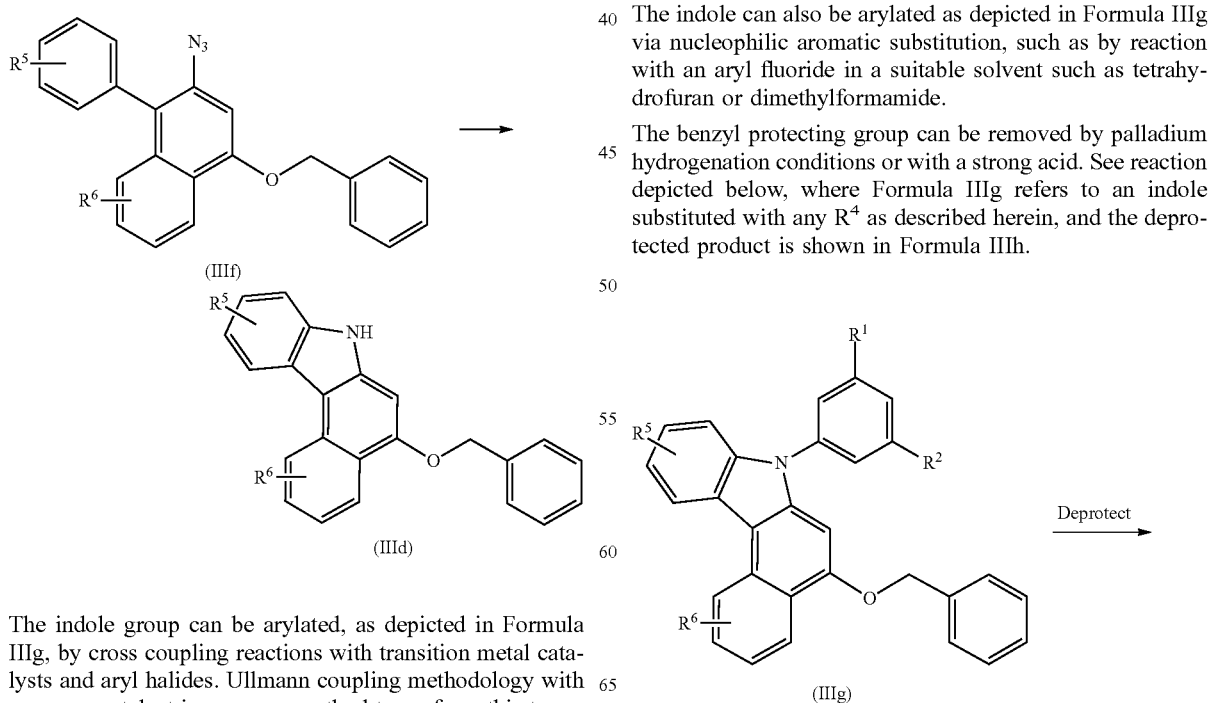

The indole group can be arylated, as depicted in Formula IIIg, by cross coupling reactions with transition metal catalysts and aryl halides. Ullmann coupling methodology with a copper catalyst is common method to perform this transformation. See reaction depicted below.

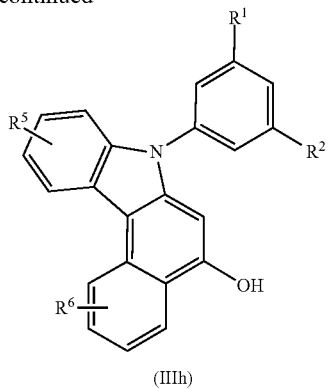

(IIIh)

The indole-fused naphthol depicted in Formula IIIh can then be reacted with aryl propargyl alcohols under acidic conditions to yield indole-fused naphthopyrans, as depicted in Formula Ia. See reaction depicted below.

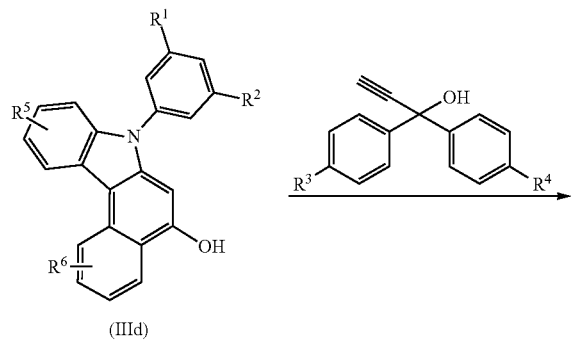

(IIId)

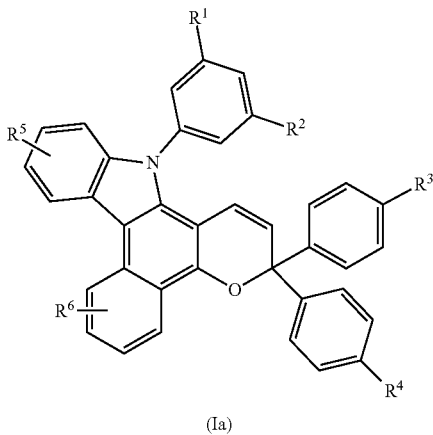

(Ia)

In accordance with the present invention there is also provided a photochromic composition, which includes at least one photochromic compound according to the present invention, such as those represented by Formula (I), (Ia), and/or (Ib) as described previously herein.

The photochromic composition can include (i) an organic material, in which the organic material is at least one of a polymeric material, an oligomeric material, or a monomeric material; and (ii) a photochromic compound according to the present invention, which is incorporated into at least a portion of the organic material. The photochromic compound can be incorporated into a portion of the organic material by methods including, but not limited to, at least one of blending or bonding the photochromic compound with the organic material or a precursor of the organic material. As used herein with reference to the incorporation of photochromic compounds into an organic material, the terms "blending" and "blended" mean that the photochromic compound/material is intermixed or intermingled with the at least a portion of the organic material, but not bonded to the organic material. Further, as used herein with reference to the incorporation of photochromic compounds into an organic material, the terms "bonding" or "bonded" mean that the photochromic compound/material is linked, such as by one or more covalent bonds, to a portion of the organic material or a precursor thereof. For example, although not limiting herein, the photochromic material can be linked to the organic material through a reactive substituent.

When the organic material is a polymeric material, the photochromic compound can be incorporated into at least a portion of the polymeric material or at least a portion of the monomeric material or oligomeric material from which the polymeric material is formed. For example, photochromic compound(s) according to the present invention that have a reactive substituent can be bonded to an organic material such as a monomer, oligomer, or polymer having a group with which a reactive moiety may be reacted, or the reactive moiety can be reacted as a co-monomer in the polymerization reaction from which the organic material is formed, for example, in a co-polymerization process.

As discussed above, the photochromic compositions according to present invention can include an organic material chosen from a polymeric material, an oligomeric material and/or a monomeric material, with some embodiments. Examples of polymeric materials that can be used with the photochromic compositions of the present invention include, but are not limited to: poly(carbonate), copolymers of ethylene and vinyl acetate; copolymers of ethylene and vinyl alcohol; copolymers of ethylene, vinyl acetate, and vinyl alcohol (such as those that result from the partial saponification of copolymers of ethylene and vinyl acetate); cellulose acetate butyrate; poly(urethane); poly(acrylate); poly(methacrylate); epoxies; aminoplast functional polymers; poly(anhydride); poly(urea urethane); N-alkoxymethyl (meth)acrylamide functional polymers; poly(siloxane); poly(silane); and combinations and mixtures thereof. Further classes and examples of polymeric materials that can be used with the photochromic compositions of the present invention include, but are not limited to, those disclosed at column 39, line 45 through column 40, line 67 of U.S. Pat. No. 9,028,728 B2.

The photochromic composition of the present invention can include at least one of, a complementary photochromic material (including one or more of those other photochromic materials and compounds described previously herein), a photoinitiator, a thermal initiator, a polymerization inhibitor, a solvent, a light stabilizer, a heat stabilizer, a mold release agent, a rheology control agent, a leveling agent, a free radical scavenger, and/or an adhesion promoter.

The photochromic composition according to the present invention can be a photochromic coating composition. Photochromic coating compositions of the present invention can include: a photochromic compound according to the present invention, such as described previously herein with regard to Formulas (I), (Ia), and/or (Ib); a resin composition that is optionally curable; and optionally a solvent. The photochromic coating composition can be in the form of art-recognized liquid coatings and powder coatings. The photochromic coating compositions of the present invention can be thermoplastic or thermosetting coating compositions. The photochromic coating composition can be a curable or thermosetting coating composition.

The curable resin composition of the curable photochromic coating compositions according to the present invention can include: a first reactant (or component) having functional groups, e.g., an epoxide functional polymer reactant; and a second reactant (or component) that is a crosslinking agent having functional groups that are reactive towards and that can form covalent bonds with the functional groups of the first reactant. The first and second reactants of the curable resin composition of the curable photochromic coating composition can each independently include one or more functional species, and are each present in amounts sufficient to provide cured photochromic coatings having a desirable combination of physical properties, e.g., smoothness, optical clarity, solvent resistance, and hardness.

Examples of curable resin compositions that can be used with the curable photochromic coating compositions according to the present invention include, but are not limited to: curable resin compositions including epoxide functional polymer (e.g., (meth)acrylic polymers containing residues of glycidyl (meth)acrylate) and epoxide reactive crosslinking agent (e.g., containing active hydrogens, such as hydroxyls, thiols and amines); and curable resin compositions including active hydrogen functional polymer (e.g., hydroxy, thiol, and/or amine functional polymer) and capped (or blocked) isocyanate functional crosslinking agent. By "capped (or blocked) isocyanate functional crosslinking agent" is meant a crosslinking agent having two or more capped isocyanate groups that can decap (or deblock) under cure conditions (e.g., at elevated temperature) to form free isocyanate groups and free capping groups. The free isocyanate groups formed by decapping of the crosslinking agent are preferably capable of reacting and forming substantially permanent covalent bonds with the active hydrogen groups of the active hydrogen functional polymer (e.g., with the hydroxy groups of a hydroxy functional polymer). Further examples of curable resin compositions that can be used with the curable photochromic coating compositions according to the present invention include, but are not limited to, those disclosed in: paragraphs [0176] through [0190] of WO 2016/142496 A1; and paragraphs [0005], [0037] through [0051], [0056] through [0059], and [0063] through [0065] of WO 2017/030545 A1.

Curable photochromic coating compositions according to the present invention can, optionally, contain additives such as waxes for flow and wetting, flow control agents, e.g., poly(2-ethylhexyl)acrylate, adjuvant resin to modify and optimize coating properties, antioxidants and ultraviolet (UV) light absorbers. Examples of useful antioxidants and UV light absorbers include those available commercially from BASF under the trademarks IRGANOX and TINUVIN. These optional additives, when used, are typically present in amounts up to 20 percent by weight (e.g., from 0.5 to 10 percent by weight), based on total weight of resin solids of the curable resin composition.

Photochromic compositions, photochromic articles and photochromic coating compositions according to the present invention can further include art-recognized additives that aid or assist in the processing and/or performance of the compositions or articles. Non-limiting examples of such additives include photoinitiators, thermal initiators, polymerization inhibitors, solvents, light stabilizers (such as, but not limited to, ultraviolet light absorbers and light stabilizers, such as hindered amine light stabilizers (HALS)), heat stabilizers, mold release agents, rheology control agents, leveling agents (such as, but not limited to, surfactants), free radical scavengers, adhesion promoters (such as hexanediol diacrylate and coupling agents), and combinations and mixtures thereof.

The photochromic compounds of the present invention can be used in amounts (or ratios) such that the compositions, organic material or substrate (e.g., photochromic articles and photochromic coatings) into which the photochromic compounds are incorporated or otherwise connected exhibits desired optical properties. The amount and types of photochromic material can be selected such that the composition, organic material or substrate is clear or colorless when the photochromic compound is in the closed-form (e.g., in the bleached or unactivated state), and can exhibit a desired resultant color when the photochromic compound (such as a photochromic indolenaphthopyran of the present invention) is in the open-form (e.g., when activated by actinic radiation). The precise amount of the photochromic material that is utilized in the various photochromic compositions and articles described herein is not critical provided that a sufficient amount is used to produce the desired effect. The particular amount of the photochromic material used can depend on a variety of factors, such as but not limited to, the absorption characteristics of the photochromic compound, the color and intensity of the color desired upon activation, and the method used to incorporate or connect the photochromic material to the substrate. Photochromic compositions according to the present invention can include the photochromic compound according to the present invention, including the compounds represented by Formula (I), (Ia), or (Ib), in an amount of from 0.01 to 40 weight percent, such as from 0.05 to 15 weight percent, such as from 0.1 to 5 weight percent, based on the weight of the photochromic composition. For purposes of further non-limiting illustration, the amount of the photochromic compound/material including the compounds represented by Formula (I), (Ia), or (Ib) that is incorporated into an organic material can range from 0.01 to 40 weight percent, such as from 0.05 to 15 weight percent, such as from 0.1 to 5 weight percent, based on the weight of the organic material.

The present invention also relates to photochromic articles that include one or more photochromic compounds according to the present invention, such as represented by Formula (I), (Ia), or (Ib). The photochromic articles can be prepared by art-recognized methods, such as by imbibition methods, cast-in-place methods, coating methods, in-mold coating methods, over-mold methods, and lamination methods.

For example, the photochromic articles can be selected from ophthalmic articles, display articles, windows, mirrors, active liquid crystal cell articles, and passive liquid crystal cell articles.

For example, the photochromic articles of the present invention can be ophthalmic articles, and the ophthalmic articles can be selected from corrective lenses, non-corrective lenses, contact lenses, intra-ocular lenses, magnifying lenses, protective lenses, and visors.

For example, the photochromic articles of the present invention can be display articles, and the display articles can be selected from screens, monitors, and security elements.

Such photochromic articles, e.g., photochromic lenses, can transition from a first unactivated state (e.g., clear and non-blue blocking state) to a second activated state (e.g., colored and blue-blocking state) upon exposure to actinic radiation. The articles revert back to the first unactivated (and clear) state upon removal of the actinic radiation source. Thus, the photochromic articles according to the present invention provide enhanced protection from health risks associated with blue light exposure during outdoor activity, while maintaining acceptable aesthetics indoors.

The present invention is more particularly described in the following examples, which are intended as illustrative only, since numerous modifications and variations therein will be apparent to those skilled in the art.

EXAMPLES

The following examples are provided to illustrate photochromic compounds of the invention, particularly the improved bleach color of photochromic compounds of the invention. Part 1 provides descriptions of the synthesis of photochromic compounds of the invention. Part 2 provides an evaluation of the photochromic performance of the photochromic compounds of the invention versus comparative photochromic compounds.

Part 1: Synthesis of Photochromic Compounds

Example 1

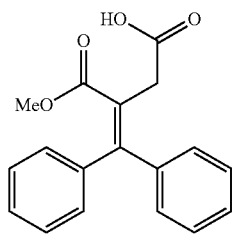 [SMILES: COC(=O)C(CC(=O)O)=C(c1ccccc1)c1ccccc1]

Step 1

While stirring under nitrogen, benzophenone (84.0 g, 461 mmol) and dimethyl succinate (80.84 g, 553 mmol) were dissolved in toluene (1.0 L). Potassium t-pentoxide (1.7 M in toluene, 352.5 mL, 599 mmol) was added dropwise over 2 hours at room temperature. After 20 hours, water (1.5 L) was added to the reaction mixture and the layers were allowed to separate. The organic phase was discarded. The aqueous phase was extracted with toluene (1×200 ml) and organic phase was discarded. The aqueous phase was acidified with 2N hydrochloric acid solution to pH 4 and the solution became turbid. The product was isolated by extracting the mixture with ethyl acetate (3×300 ml). The organic layers were combined, dried with sodium sulfate and concentrated under reduced pressure. The resultant solid was washed with hexanes, collected and dried under vacuum to give 132.8 g (97% yield) of a colorless powder.

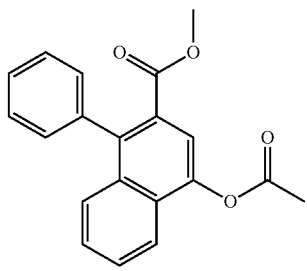 [SMILES: COC(=O)c1cc(OC(C)=O)c2ccccc2c1-c1ccccc1]

Step 2

While stirring under nitrogen, the product from Step 1 (132.8 g, 448.2 mmol) was combined with acetic anhydride (254.2 mL, 2.69 mol) and toluene (250 ml) and heated to reflux. After 16 hours, the reaction mixture was concentrated under reduced to pressure and the resultant oil was precipitated in hexanes to give an off-white solid. The solid was collected and dried to give 125.5 g (88% yield).

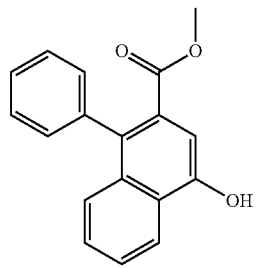 [SMILES: COC(=O)c1cc(O)c2ccccc2c1-c1ccccc1]

Step 3

The product from Step 2 (150 g, 468 mmol) was suspended in methanol (400 ml) with stirring. Concentrated hydrochloric acid (10 ml) was added to the suspension and the reaction mixture was heated to reflux for 2 hours. Once complete, the reaction mixture was allowed to cool to room temperature and sit without stirring for 50 hours as the product recrystallized. The crystals were collected and dried to give complete conversion (130 g).

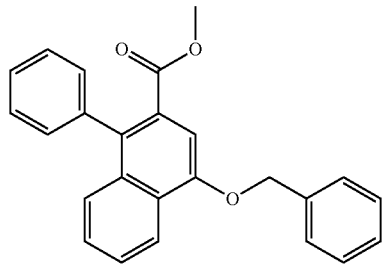 [SMILES: COC(=O)c1cc(OCc2ccccc2)c2ccccc2c1-c1ccccc1]

Step 4

While stirring under nitrogen, the product from Step 3 (130 g, 467 mmol) was dissolved in anhydrous dimethylformamide (400 ml). Potassium carbonate (130 g, 934 mmol) was suspended in the mixture followed by the slow addition of benzyl chloride (71.0 g, 560 mmol). The reaction mixture was heated at 75° C. for 16 hours. Once cool, the reaction mixture was slowly poured into ice water and extracted into ethyl acetate (3×500 ml). The organic layers were combined, washed with brine (2×300 ml), dried with sodium sulfate and concentrated under reduced pressure. The resulting solid was washed with methanol, collected and dried under vacuum to give a colorless solid (155.4 g, 90% yield).

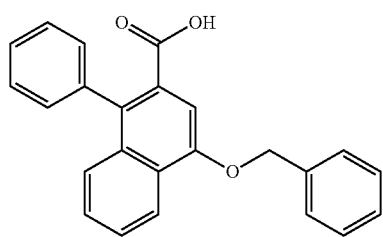 [SMILES: O=C(O)c1cc(OCc2ccccc2)c2ccccc2c1-c1ccccc1]

Step 5

The product from Step 4 (155.4 g, 422 mmol) was suspended in 2-propanol (300 ml) with stirring. Sodium hydroxide solution (10% w/w in water, 300 ml) was added and the reaction mixture was heated to reflux for 18 hours. Once cool, the reaction mixture was poured into an acidic ice water bath (pH 3-4) to form a colorless precipitate. The powder was collected and dried to give 148.9 g (99% yield).

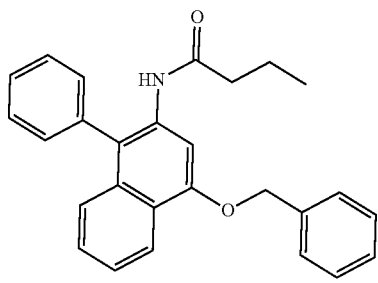 [SMILES: CCCC(=O)Nc1cc(OCc2ccccc2)c2ccccc2c1-c1ccccc1]

Step 6

While stirring under nitrogen, the product from Step 5 (149.1 g, 421 mmol) was suspended in anhydrous toluene (800 ml). Triethylamine (111 g, 1.1 mol) and absolute ethanol (100 ml) were added dissolving the suspension. Diphenylphosphoryl azide (174 g, 632 mmol) was added portion-wise to the reaction mixture that exothermed to reflux on its own accord and heat was added to reflux for a total of 2 hours. Once cool, the reaction mixture was added to water (1.5 L) and ethyl acetate (500 ml) and the layers were separated. The organic layer was washed with water (3×1 L), dried with sodium sulfate and concentrated under reduced pressure to give a reddish oil that was used without further purification.

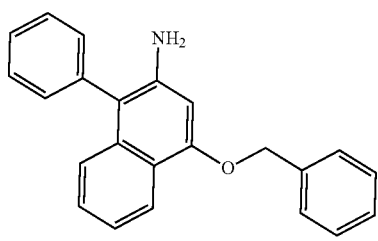 [SMILES: Nc1cc(OCc2ccccc2)c2ccccc2c1-c1ccccc1]

Step 7

The resultant oil from Step 6 was dispersed in tetrahydrofuran (600 ml), ethanol (400 ml) and water (1.1 L) with sodium hydroxide (86 g, 2.2 mol). The reaction mixture was heated to reflux for 5 days. Once cool, brine (200 ml) was added to the reaction mixture, the layers were separated and the aqueous layer was washed with ethyl acetate (3×300 ml). The organic layers were combined, dried with sodium sulfate and concentrated under reduced pressure to give a reddish semi-solid that was used without further purification.

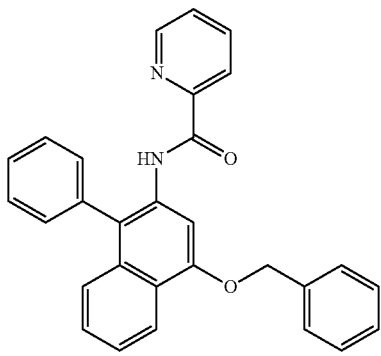 [SMILES: O=C(Nc1cc(OCc2ccccc2)c2ccccc2c1-c1ccccc1)c1ccccn1]

Step 8

While stirring under nitrogen, the product from Step 7 was taken up in dichloromethane (1.2 L). Picolinic acid (78 g, 632 mmol) and 4-(dimethlyamino)pyridine (5.2 g, 42 mmol) were added followed by N,N'-dicyclohexylcarbodiimide (130.4 g, 632 mmol). The reaction mixture was allowed to stir at room temperature for 16 hours. The reaction mixture was filtered and concentrated under reduced pressure to give a black solid that was washed with methanol to give Intermediate 2 as an off-white powder (160.85 g, 89% yield for 3 steps).

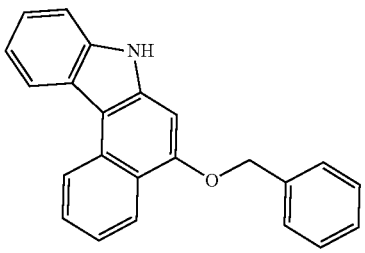 [SMILES: c1ccc(COc2cc3[nH]c4ccccc4c3c3ccccc23)cc1]

Step 9

While stirring under nitrogen, the product from step 8 (76.5 g, 178 mmol) was dissolved in anhydrous dimethylformamaide (500 ml) and to this was added copper (II) acetate (65.0 g, 356 mmol) and glacial acetic acid (10.7 g, 178 mmol). The reaction mixture was heated to 150° C. for 20 hours to give 70% conversion of the starting material. The reaction mixture was filtered over a celite pad and the pad was washed with 500 ml of ethyl acetate. The filtrate was added to separatory funnel with water (1.0 L) containing ethylenediamine (10 ml) and the layers were separated. The organic layer was washed with water (3×300 ml), dried with sodium sulfate and concentrated under reduced pressure to give an off-white solid. The material was subjected to a second iteration of the reaction conditions and same isolation procedures. The resulting solid was washed twice with methanol (300 ml) to give an off-white powder (49.5 g 86% yield). The product was confirmed by $^1$H NMR and mass spectroscopy.

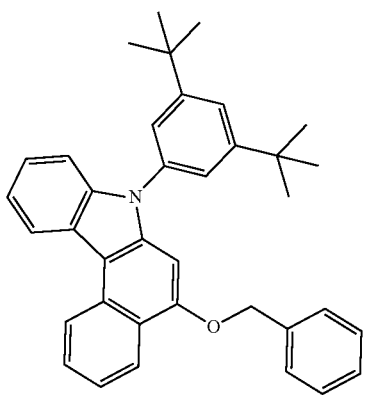 [SMILES: CC(C)(C)c1cc(-n2c3ccccc3c3c4ccccc4c(OCc4ccccc4)cc32)cc(C(C)(C)C)c1]

Step 10

While stirring under nitrogen, the product from Step 9 (4.0 g, 12.4 mmol) was combined with 3,5-di-tert-butylbromobenzene (6.73 g, 25.0 mmol), copper iodide (1.20 g, 6.2 mmol), potassium carbonate (3.42 g, 24.8 mmol), 1,10-phenanthroline (0.45 g, 2.5 mmol) and dibenzo-18-crown-6-ether (0.45 g, 1.20 mmol) in anhydrous dimethylformamide (30 ml). The reaction mixture was heated to 150° C. for 4 hours. Once cool, the reaction mixture was taken up in ethyl acetate (250 ml) and washed initially with water (200 ml) with ethylene diamine (10 ml) followed by water (2×250 ml). The organic layer was dried with sodium sulfate and concentrated under reduced pressure onto silica gel. Chromatography (silica gel, 0-50% dichloromethane in hexanes) yielded a colorless powder that was washed with methanol and dried under vacuum (5.44 g, 86% yield).

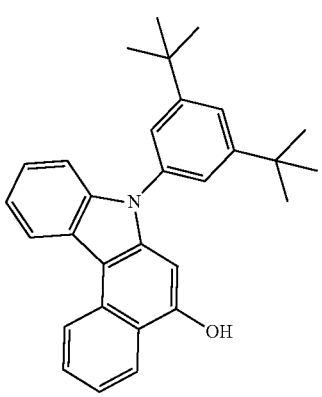 [SMILES: CC(C)(C)c1cc(-n2c3ccccc3c3c4ccccc4c(O)cc32)cc(C(C)(C)C)c1]

Step 11

While stirring under nitrogen, the product from Step 10 (2.0 g, 3.91 mmol) was combined with ammonium formate (2.52 g, 40.0 mmol) and palladium on carbon (Degussa type E1003 U/W, 0.14 g, 1.2 mmol) in dimethylformamide (30 ml). The reaction mixture was heated to 80° C. for 3 hours. Once cool, the reaction mixture was filtered over a pad of celite and the pad was washed with ethyl acetate (250 ml). The filtrate was washed with water (3×300 ml), dried with sodium sulfate and concentrated under reduced pressure to give a brown glass used without further purification. (A powder could be afforded if precipitated from dichloromethane into hexanes.)

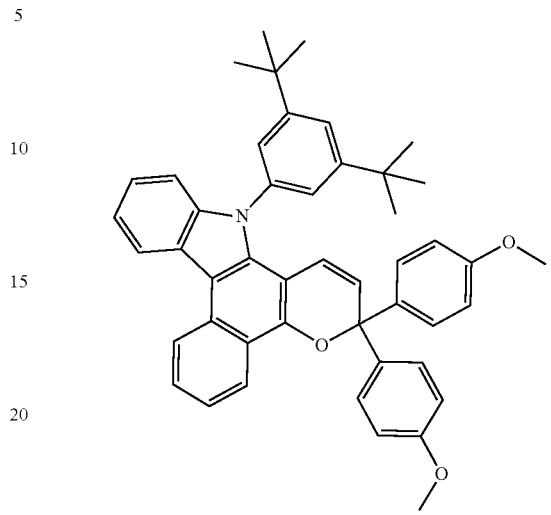

Step 12

While stirring under nitrogen, the product from Step 11 (0.80 g, 1.90 mmol) was combined with 1,1-bis(4-methoxyphenyl)prop-2-yn-1-ol (0.55 g, 2.3 mmol) in toluene (25 ml) and heated towards reflux. p-Toluenesulfonic acid (5-10 mg) was added and the reaction mixture was heated to reflux for 1 hour. Once cool, the reaction mixture was concentrated under reduced pressure onto silica gel. Chromatography (silica gel, 0-70% dichloromethane in hexanes) yielded a dark solid. The product was recrystallized twice from tetrahydrofuran, methyl tert-butylether and methanol to give Example 11 as light yellow powder (1.14 g, 89% yield) and confirmed by mass spectrometry.

Examples 2-21 and Comparable Examples 1-11

Additional photochromic dyes were prepared according to Example 1 and are summarized in Table 3. For each example, an appropriate substituted phenyl bromide was used in place of 3,5-di-tert-butyl bromobenzene in Example 1, Step 10 indicated in the N-Coupling Component column in Table 3. An appropriate substituted 1,1-diphenylprop-2-yn-1-ol ("propargyl alcohol") was used in Example 1, Step 12 indicated in the Propargyl Alcohol column in Table 3. Comparable Examples 4, 8 and 11 were prepared by alkylation of the product of Example 1, Step 9 using sodium hydride and methyl iodide in anhydrous dimethylformamide. All products were confirmed by mass spectrometry.

TABLE 3

| Example # | Structure | N-Coupling component | Yield[1] (%) | Propargyl Alcohol | Yield[2] (%) |
|---|---|---|---|---|---|
| 1 | 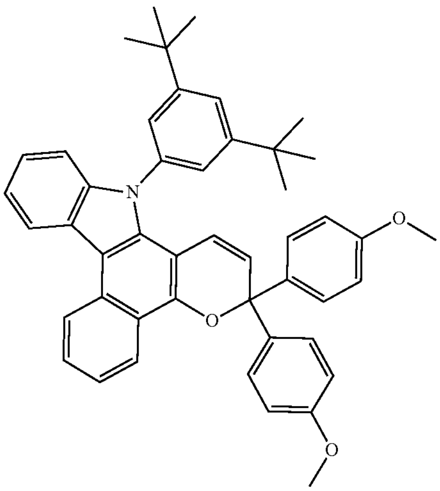 [SMILES: COc1ccc(C2(c3ccc(OC)cc3)C=Cc3c(c4ccccc4c4c5ccccc5n(-c5cc(C(C)(C)C)cc(C(C)(C)C)c5)c34)O2)cc1] | | 86 | | 89 |
| 2 | 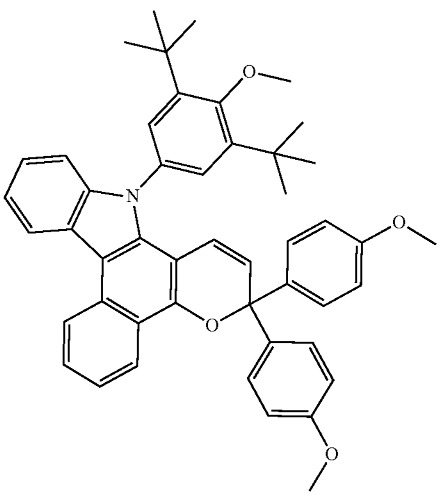 [SMILES: COc1ccc(C2(c3ccc(OC)cc3)C=Cc3c(c4ccccc4c4c5ccccc5n(-c5cc(C(C)(C)C)c(OC)c(C(C)(C)C)c5)c34)O2)cc1] | | 74 | | 45 |
| 3 | 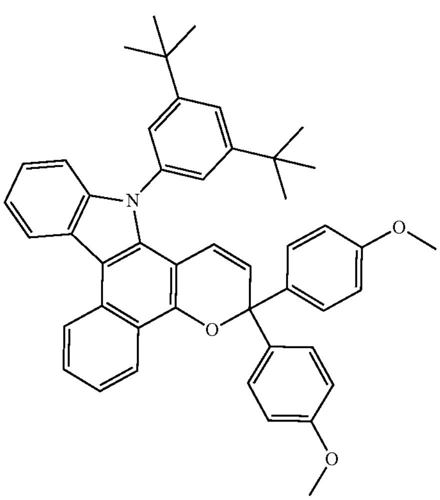 [SMILES: COc1ccc(C2(c3ccc(OC)cc3)C=Cc3c(c4ccccc4c4c5ccccc5n(-c5cc(C(C)(C)C)cc(C(C)(C)C)c5)c34)O2)cc1] | | 83 | | 70 |

TABLE 3-continued

| Example # | Structure | N-Coupling component | Yield[1] (%) | Propargyl Alcohol | Yield[2] (%) |
|---|---|---|---|---|---|
| 4 | (structure with 3,5-bis(trifluoromethyl)phenyl group) | 3,5-bis(trifluoromethyl)bromobenzene | 84 | 1,1-bis(4-methoxyphenyl)prop-2-yn-1-ol | 70 |
| 5 | (structure with 3,5-diethylphenyl group) | 3,5-diethylbromobenzene | 85 | 1,1-bis(4-methoxyphenyl)prop-2-yn-1-ol | 44 |
| 6 | (structure with 3,5-dimethylphenyl group) | 3,5-dimethylbromobenzene | 81 | 1,1-bis(4-methoxyphenyl)prop-2-yn-1-ol | 59 |

TABLE 3-continued

| Example # | Structure | N-Coupling component | Yield[1] (%) | Propargyl Alcohol | Yield[2] (%) |
|---|---|---|---|---|---|
| 7 | 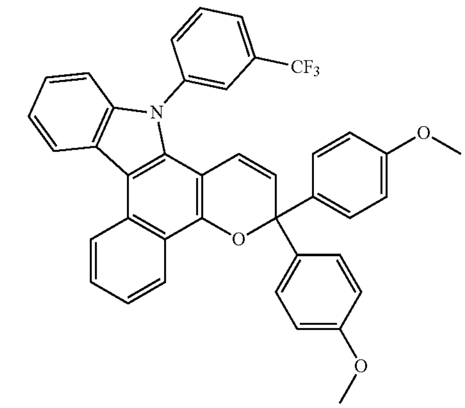 [SMILES: COc1ccc(C2(c3ccc(OC)cc3)C=Cc3c(c4ccccc4c4c5ccccc5n(-c5cccc(C(F)(F)F)c5)c34)O2)cc1] | 3-bromo-(trifluoromethyl)benzene | 75 | 1,1-bis(4-methoxyphenyl)prop-2-yn-1-ol | 64 |
| 8 | 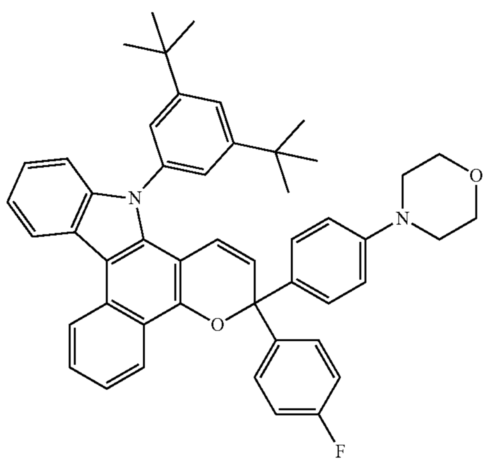 [SMILES: CC(C)(C)c1cc(-n2c3ccccc3c3c4ccccc4c4c(c32)C=CC(c2ccc(F)cc2)(c2ccc(N3CCOCC3)cc2)O4)cc(C(C)(C)C)c1] | 1-bromo-3,5-di-tert-butylbenzene | 86 | 1-(4-fluorophenyl)-1-(4-morpholinophenyl)prop-2-yn-1-ol | 59 |
| 9 | 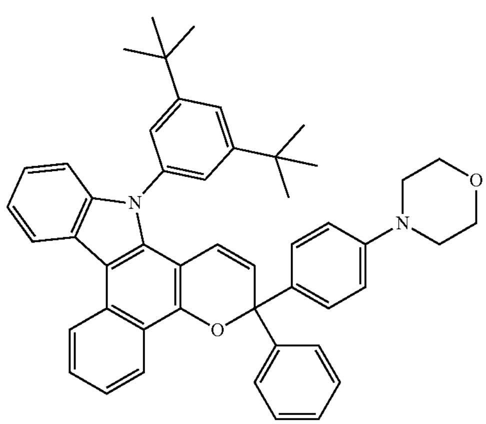 [SMILES: CC(C)(C)c1cc(-n2c3ccccc3c3c4ccccc4c4c(c32)C=CC(c2ccccc2)(c2ccc(N3CCOCC3)cc2)O4)cc(C(C)(C)C)c1] | 1-bromo-3,5-di-tert-butylbenzene | 86 | 1-(4-morpholinophenyl)-1-phenylprop-2-yn-1-ol | 77 |

TABLE 3-continued
| Example # | Structure | N-Coupling component | Yield[1] (%) | Propargyl Alcohol | Yield[2] (%) |
|---|---|---|---|---|---|
| 10 | 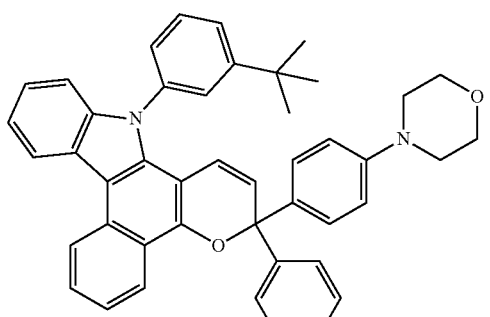 | 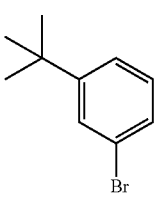 | 83 | 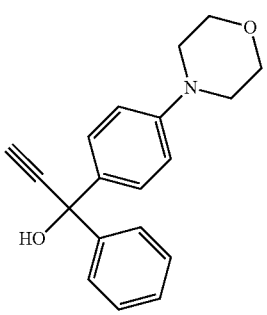 [SMILES: C#CC(O)(c1ccccc1)c1ccc(N2CCOCC2)cc1] | 90 |
| 11 | 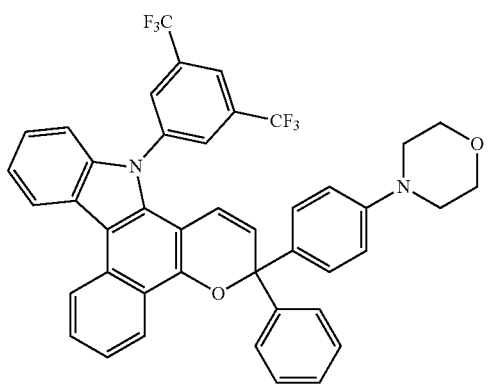 [SMILES: FC(F)(F)c1cc(-n2c3ccccc3c3c4ccccc4c4c(c32)C=CC(c2ccccc2)(c2ccc(N3CCOCC3)cc2)O4)cc(C(F)(F)F)c1] | 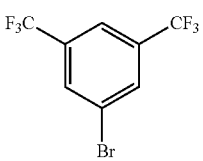 | 84 | 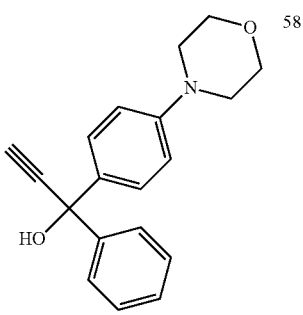 | 58 |
| 12 | 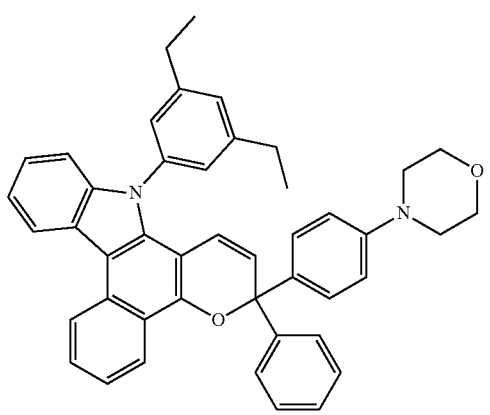 [SMILES: CCc1cc(CC)cc(-n2c3ccccc3c3c4ccccc4c4c(c32)C=CC(c2ccccc2)(c2ccc(N3CCOCC3)cc2)O4)c1] | 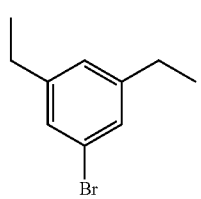 | 85 | 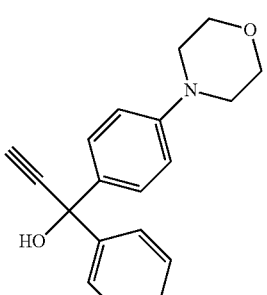 | 75 |
| 13 | 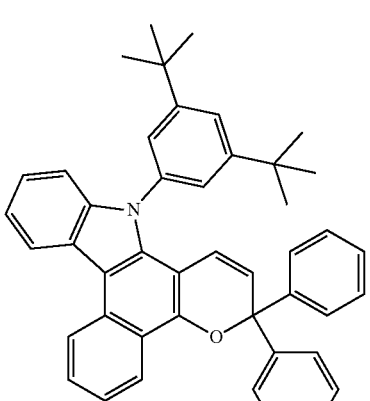 | 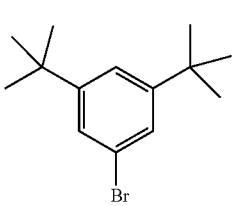 | 86 | 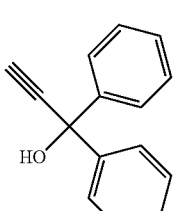 | 39 |

TABLE 3-continued

| Example # | Structure | N-Coupling component | Yield¹ (%) | Propargyl Alcohol | Yield² (%) |
|---|---|---|---|---|---|
| 14 | 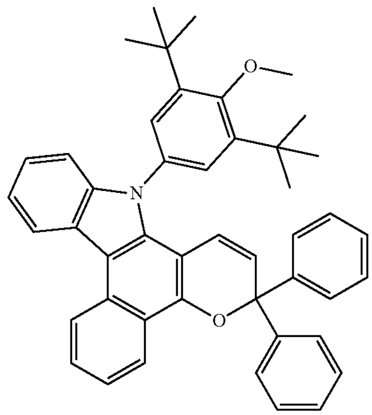 [SMILES: COc1c(C(C)(C)C)cc(-n2c3ccccc3c3c4ccccc4c4c(c32)C=CC(c2ccccc2)(c2ccccc2)O4)cc1C(C)(C)C] | | 74 | | 35 |
| 15 | 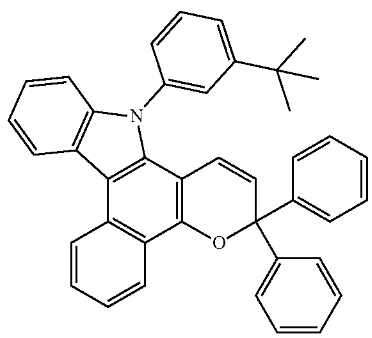 [SMILES: CC(C)(C)c1cccc(-n2c3ccccc3c3c4ccccc4c4c(c32)C=CC(c2ccccc2)(c2ccccc2)O4)c1] | | 83 | | 25 |
| 16 | 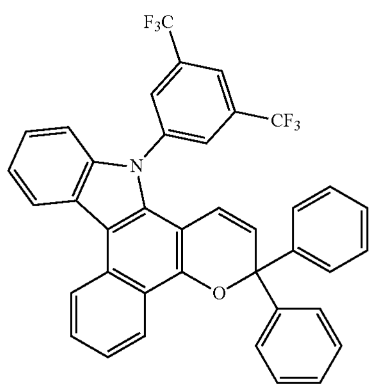 [SMILES: FC(F)(F)c1cc(-n2c3ccccc3c3c4ccccc4c4c(c32)C=CC(c2ccccc2)(c2ccccc2)O4)cc(C(F)(F)F)c1] | | 84 | | 17 |
| 17 | 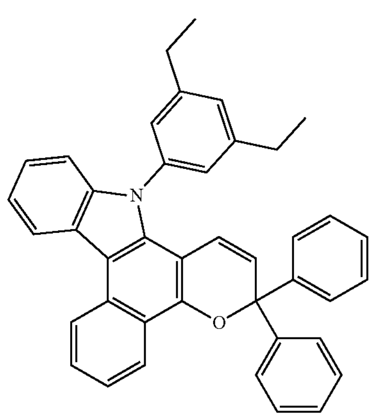 [SMILES: CCc1cc(CC)cc(-n2c3ccccc3c3c4ccccc4c4c(c32)C=CC(c2ccccc2)(c2ccccc2)O4)c1] | | 85 | | 34 |

TABLE 3-continued

| Example # | Structure | N-Coupling component | Yield[1] (%) | Propargyl Alcohol | Yield[2] (%) |
|---|---|---|---|---|---|
| 18 | 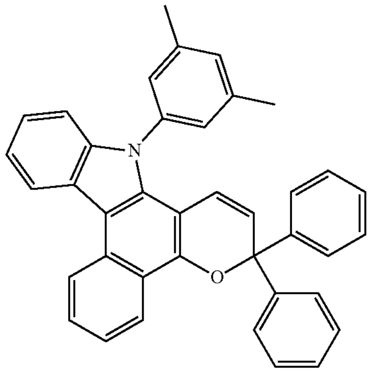 [SMILES: Cc1cc(C)cc(-n2c3ccccc3c3c4ccccc4c4c(c32)C=CC(c2ccccc2)(c2ccccc2)O4)c1] | 3,5-dimethylbromobenzene | 81 | 1,1-diphenyl-2-propyn-1-ol | 44 |
| 19 | 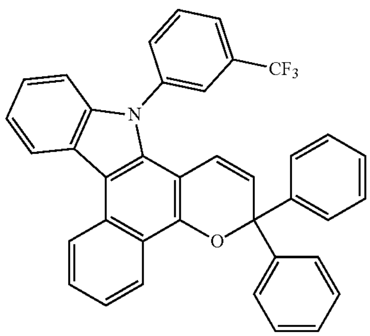 [SMILES: FC(F)(F)c1cccc(-n2c3ccccc3c3c4ccccc4c4c(c32)C=CC(c2ccccc2)(c2ccccc2)O4)c1] | 3-(trifluoromethyl)bromobenzene | 75 | 1,1-diphenyl-2-propyn-1-ol | 58 |
| 20 | 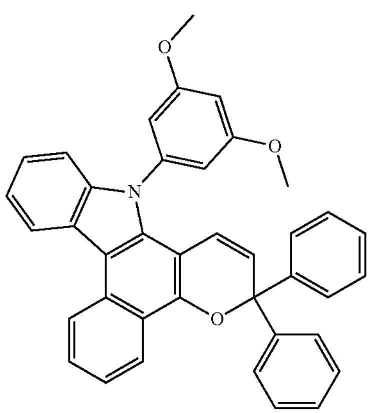 [SMILES: COc1cc(OC)cc(-n2c3ccccc3c3c4ccccc4c4c(c32)C=CC(c2ccccc2)(c2ccccc2)O4)c1] | 3,5-dimethoxybromobenzene | 88 | 1,1-diphenyl-2-propyn-1-ol | 32 |
| 21 | 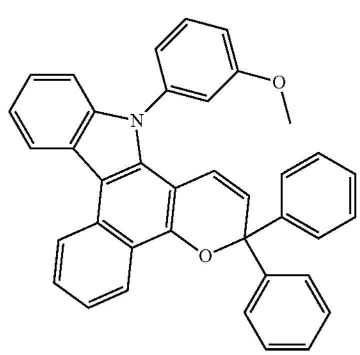 [SMILES: COc1cccc(-n2c3ccccc3c3c4ccccc4c4c(c32)C=CC(c2ccccc2)(c2ccccc2)O4)c1] | 3-methoxybromobenzene | 86 | 1,1-diphenyl-2-propyn-1-ol | 24 |

TABLE 3-continued

| Example # | Structure | N-Coupling component | Yield[1] (%) | Propargyl Alcohol | Yield[2] (%) |
|---|---|---|---|---|---|
| CE1 | 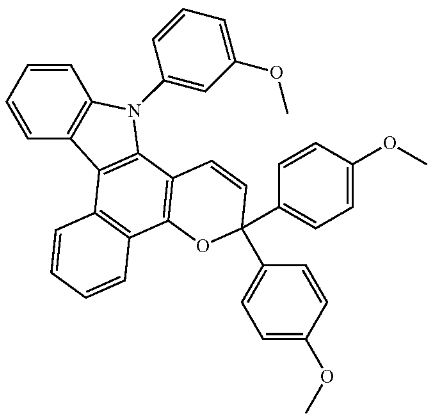 [SMILES: COc1ccc(C2(c3ccc(OC)cc3)C=Cc3c(c4ccccc4c4c5ccccc5n(-c5cccc(OC)c5)c34)O2)cc1] | 3-bromoanisole | 86 | 1,1-bis(4-methoxyphenyl)-2-propyn-1-ol | 29 |
| CE2 | 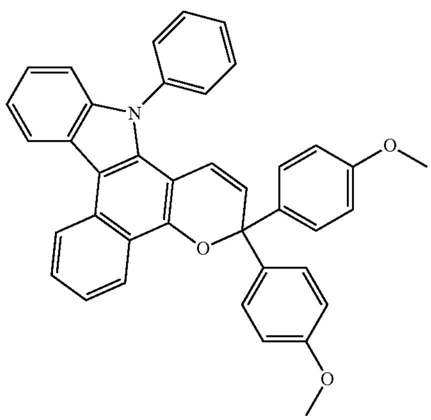 [SMILES: COc1ccc(C2(c3ccc(OC)cc3)C=Cc3c(c4ccccc4c4c5ccccc5n(-c5ccccc5)c34)O2)cc1] | bromobenzene | 66 | 1,1-bis(4-methoxyphenyl)-2-propyn-1-ol | 24 |
| CE3 | 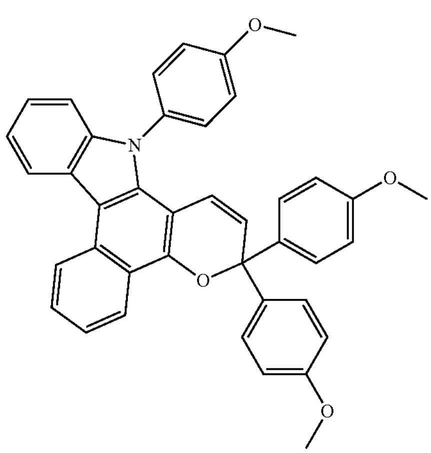 [SMILES: COc1ccc(-n2c3ccccc3c3c4ccccc4c4c(c32)C=CC(c2ccc(OC)cc2)(c2ccc(OC)cc2)O4)cc1] | 4-bromoanisole | 92 | 1,1-bis(4-methoxyphenyl)-2-propyn-1-ol | 85 |

TABLE 3-continued

| Example # | Structure | N-Coupling component | Yield[1] (%) | Propargyl Alcohol | Yield[2] (%) |
| --- | --- | --- | --- | --- | --- |
| CE4 | 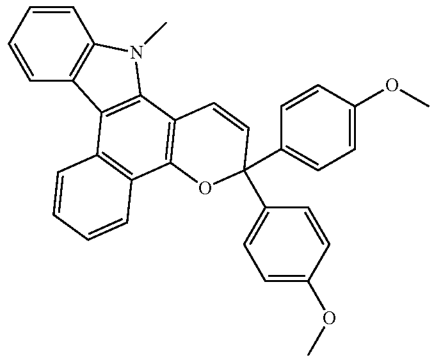 [SMILES: COc1ccc(C2(c3ccc(OC)cc3)C=Cc3c(c4ccccc4c4c5ccccc5n(C)c34)O2)cc1] | I—CH₃ | 85 | | 71 |
| CE5 | 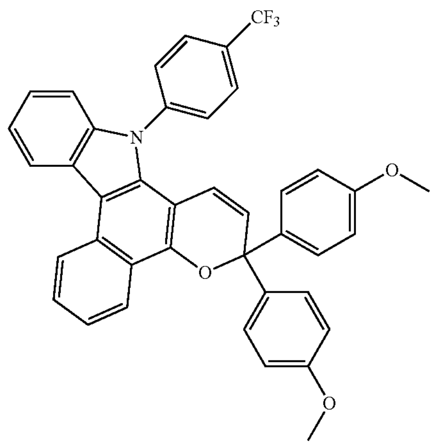 [SMILES: COc1ccc(C2(c3ccc(OC)cc3)C=Cc3c(c4ccccc4c4c5ccccc5n(-c5ccc(C(F)(F)F)cc5)c34)O2)cc1] | 4-CF₃-C₆H₄-Br | 77 | | 72 |
| CE6 | 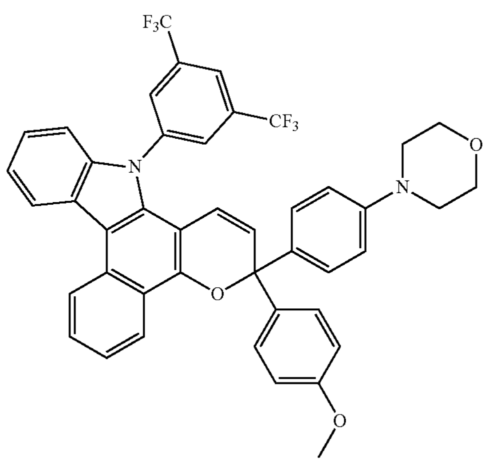 [SMILES: COc1ccc(C2(c3ccc(N4CCOCC4)cc3)C=Cc3c(c4ccccc4c4c5ccccc5n(-c5cc(C(F)(F)F)cc(C(F)(F)F)c5)c34)O2)cc1] | 3,5-(CF₃)₂-C₆H₃-Br | 84 | | 62 |
| CE7 | 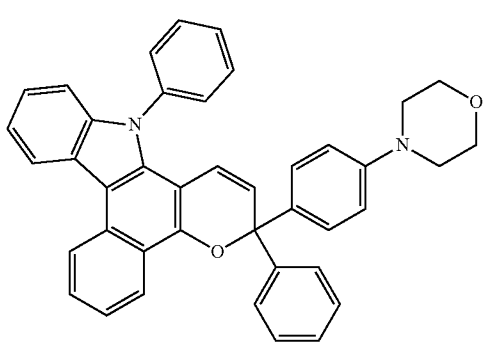 [SMILES: C1=CC(c2ccccc2)(c2ccc(N3CCOCC3)cc2)Oc2c1c1c(c3ccccc23)c2ccccc2n1-c1ccccc1] | C₆H₅-Br | 66 | | 79 |

TABLE 3-continued
| Example # | Structure | N-Coupling component | Yield[1] (%) | Propargyl Alcohol | Yield[2] (%) |
|---|---|---|---|---|---|
| CE8 | 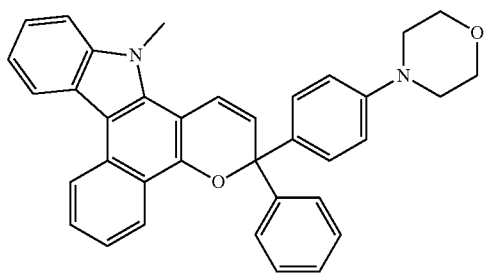 [SMILES: Cn1c2ccccc2c2c3ccccc3c3c(c21)C=CC(c1ccccc1)(c1ccc(N2CCOCC2)cc1)O3] | I—CH$_3$ | 85 | 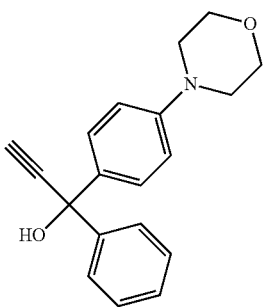 [SMILES: C#CC(O)(c1ccccc1)c1ccc(N2CCOCC2)cc1] | 74 |
| CE9 | 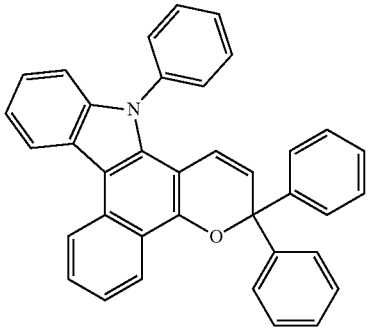 [SMILES: C1=CC(c2ccccc2)(c2ccccc2)Oc2c1c1c(c3ccccc23)c2ccccc2n1-c1ccccc1] | 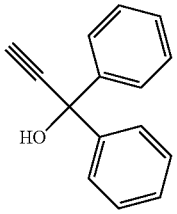 | 66 | 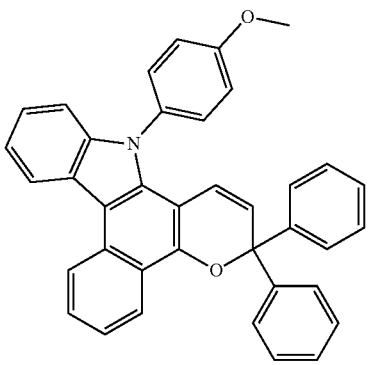 [SMILES: COc1ccc(-n2c3ccccc3c3c4ccccc4c4c(c32)C=CC(c2ccccc2)(c2ccccc2)O4)cc1] | 27 |
| CE10 | 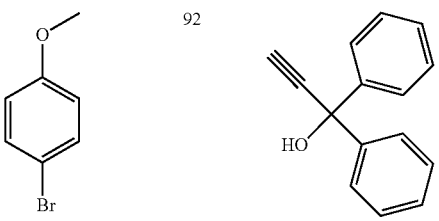 | 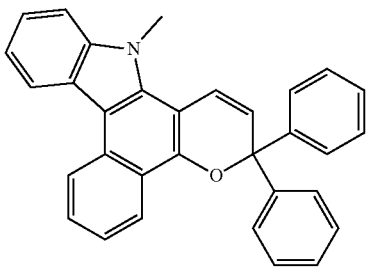 | 92 | 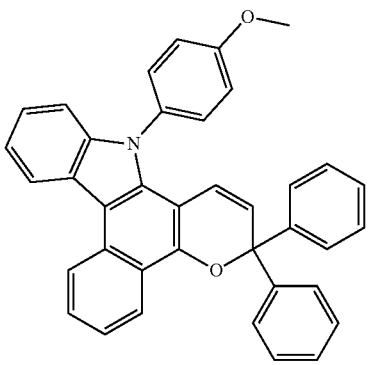 [SMILES: COc1ccc(-n2c3ccccc3c3c4ccccc4c4c(c32)C=CC(c2ccccc2)(c2ccccc2)O4)cc1] | 27 |
| CE11 | 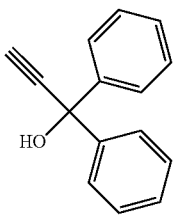 [SMILES: C#CC(O)(c1ccccc1)c1ccccc1] | I—CH$_3$ | 85 | 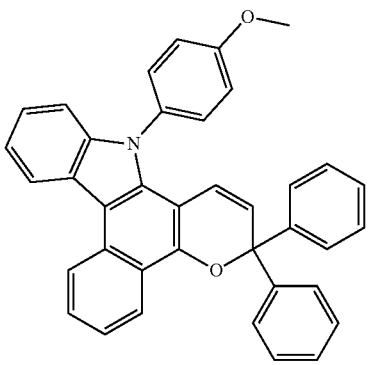 [SMILES: COc1ccc(-n2c3ccccc3c3c4ccccc4c4c(c32)C=CC(c2ccccc2)(c2ccccc2)O4)cc1] | 36 |
[1]Yield corresponds to isolated intermediate prior to deprotection and propargyl alcohol addition (Formula IIIg).
[2]Yield corresponds to isolated dye compound (Formula Ia).

Examples 22-24 and CE12

Additional photochromic dyes were prepared according to Example 1 except that 4-4'-dimethylbenzophenone was used instead of benzophenone in Example 1, Step 1 and are summarized in Table 4. For each example, an appropriate substituted phenyl bromide is indicated in the N-Coupling Component column in Table 4. An appropriate substituted 1,1-diphenylprop-2-yn-1-ol ("propargyl alcohol") was also used as indicated in the Propargyl Alcohol column in Table 4. All products were confirmed by mass spectrometry.

TABLE 4

| Example # | Structure | N-Coupling component | Yield[1] (%) | Propargyl Alcohol | Yield[2] (%) |
|---|---|---|---|---|---|
| 22 | 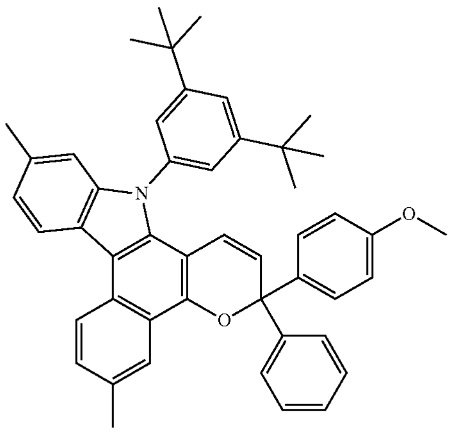 | | 80 | | 64 |
| 23 | 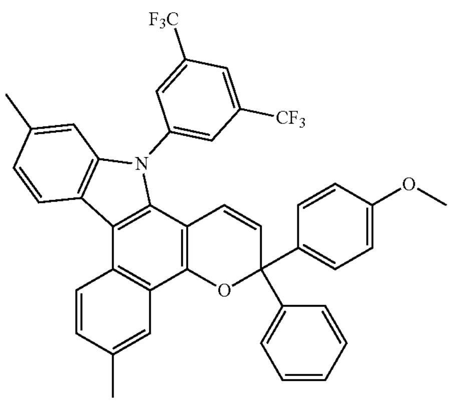 | | 53 | | 70 |
| 24 | 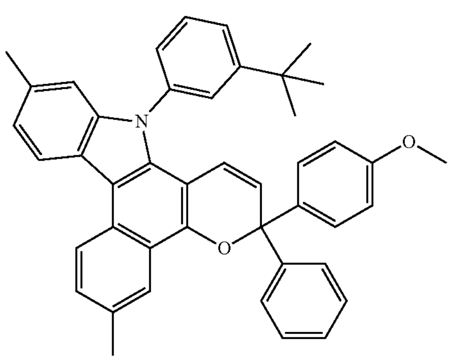 | | 55 | | 63 |

TABLE 4-continued

| Example # | Structure | N-Coupling component | Yield[1] (%) | Propargyl Alcohol | Yield[2] (%) |
|---|---|---|---|---|---|
| CE12 | 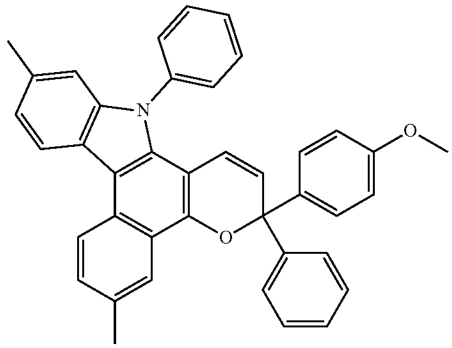 | | 99 | | 50 |

Example 25 and CE13

Additional photochromic dyes were prepared according to Example 1 except that 4-methoxybenzophenone was used instead of benzophenone in Example 1, Step 1 and are summarized in Table 5. For each example, an appropriate substituted phenyl bromide is indicated in the N-Coupling Component column in Table 5. An appropriate substituted 1,1-diphenylprop-2-yn-1-ol ("propargyl alcohol") was also used as indicated in the Propargyl Alcohol column in Table 5. All products were characterized by mass spectrometry.

Examples 26-27 and CE14

Additional photochromic dyes were prepared according to Example 1 except that (3,4-dimethoxyphenyl)(4-(trifluoromethyl)phenyl)methanone was used instead of benzophenone in Example 1, Step 1 and are summarized in Table 6. For each example, an appropriate substituted phenyl bromide is indicated in the N-Coupling Component column in Table 6. An appropriate substituted 1,1-diphenylprop-2-yn-1-ol ("propargyl alcohol") was also used as indicated in the

TABLE 5

| Example # | Structure | N-Coupling component | Yield[1] (%) | Propargyl Alcohol | Yield[2] (%) |
|---|---|---|---|---|---|
| 25 | 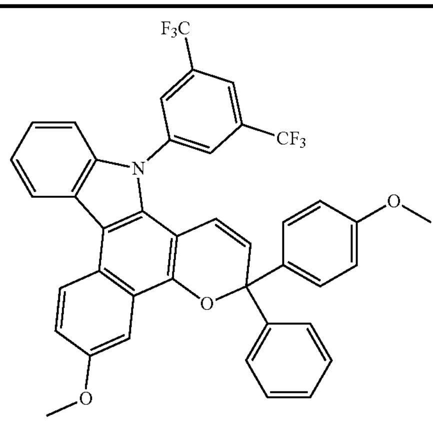 | | 78 | | 74 |
| CE13 | 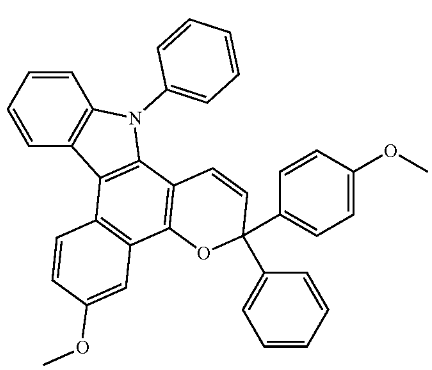 [SMILES: COc1ccc(C2(c3ccccc3)C=Cc3c(c4cc(OC)ccc4c4c5ccccc5n(-c5ccccc5)c34)O2)cc1] | | 82 | | 76 |

Propargyl Alcohol column in Table 6. All products were characterized by mass spectrometry.

TABLE 6

| Example # | Structure | N-Coupling component | Yield[1] (%) | Propargyl Alcohol | Yield[2] (%) |
|---|---|---|---|---|---|
| 26 | (structure shown) | (structure shown) | 88 | (structure shown) | 84 |
| 27 | (structure shown) | (structure shown) | 90 | (structure shown) | 52 |
| CE14 | (structure shown) | (structure shown) | 93 | (structure shown) | 65 |

Part 2: Evaluation of Photochromic Dyes

Each of the photochromic dyes from Examples 1 through 27, and each comparative example CE1 to CE14 were incorporated into a polyurethane coating system as described in U.S. Pat. No. 8,608,988 examples 1-3 at the same mol % and applied at the same coating thickness to 2"×2" test chips made from CR-39® monomer (PPG Industries, Inc.). All coated test chips were cured at 125° C. for 1 hour.

Each of the coated test chips was conditioned by first being exposed to 365-nanometer ultraviolet light for 10 minutes at a distance of about 14 centimeters to activate the photochromic materials within the coating. The UVA (315 to 380 nm) irradiance at the chip was measured with a LICOR® Model Li-1800 spectroradiometer and found to be 22.2 watts per square meter. Each of the test chips was then placed under a 500 watt, high intensity halogen lamp for 10 minutes at a distance of about 36 centimeters to bleach (inactivate) the photochromic materials. The illuminance at chip was measured with the LICOR® spectroradiometer and found to be 21.9 Klux. The coated test chips then were kept in a dark environment at room temperature (i.e., from 70 to 75° F., or 21 to 24° C.) for at least 1 hour prior to testing on an optical bench. Prior to optical bench measurement, the coated test chips were measured for ultraviolet absorbance at 390 nanometers.

Percent transmission (% T) for Examples 1 through 27, and for each comparative example CE1 through CE14 was determined using the CIE Y value in accordance with CIE 15: 2004 colorimetry using a D 65 illuminant and 10° observer. The a* and b* values as used herein in the specification and the claims refers to the a* and b* values measured in accordance with in accordance with CIE 15: 2004 space colorimetry, employing a D 65 illuminant and 10° observer, using the Hunter UltraScan Pro unit.

The BMP optical bench was fitted with two 150-watt ORIEL® Model #66057 Xenon arc lamps at right angles to each other. The light path from Lamp 1 was directed through a 3 mm SCFIOTT® KG-2 band-pass filter and appropriate neutral density filters that contributed to the required UV and partial visible light irradiance level. The light path from Lamp 2 was directed through a 3 mm SCFIOTT® KG-2 band-pass filter, a SCFIOTT® short band 400 nm cutoff filter and appropriate neutral density filters in order to provide supplemental visible light illuminance. A 2 inch×2 inch 50% polka dot beam splitter, at 450 to each lamp is used to mix the two beams. The combination of neutral density filters and voltage control of the Xenon arc lamp were used to adjust the intensity of the irradiance. Proprietary software i.e., BMPSoft version 2.1e was used on the BMP to control timing, irradiance, air cell and sample temperature, shuttering, filter selection and response measurement. A ZEISS® spectrophotometer, Model MCS 501, with fiber optic cables for light delivery through the coated test chip was used for response and color measurement. Photopic response measurements were collected on each coated test chip. The power output of the optical bench, i.e., the dosage of light that the coated test chip was exposed to, was adjusted to 6.7 Watts per square meter ($W/m^2$) UVA, integrated from 315-380 nm and 50 Klux illuminance, integrated from 380-780 nm. Measurement of this power setpoint was made using an irradiance probe and the calibrated Zeiss spectrophotometer. The coated test chip sample cell was fitted with a quartz window and self-centering sample holder. The temperature in the sample cell was controlled at 23° C. through the software with a modified Facis, Model FX-10, environment simulator. Measurement of the sample's dynamic photochromic response and color measurements was made using the same Zeiss spectrophotometer, with fiber optic cables for light delivery from a tungsten halogen lamp and through the sample. The collimated monitoring light beam from the fiber optic cable was maintained perpendicular to the test sample while passing through the sample and directed into a receiving fiber optic cable assembly attached to the spectrophotometer. The exact point of placement of the sample in the sample cell was where the activating xenon arc beam and the monitoring light beam intersected to form two concentric circles of light. The angle of incidence of the xenon arc beam at the sample placement point was =300 from perpendicular.

Response measurements, in terms of a change in optical density ($\Delta OD$) from the unactivated or bleached state to the activated or colored state were determined by establishing the initial unactivated transmittance, opening the shutter from the Xenon lamp(s) and measuring the transmittance through activation at selected intervals of time. The change in optical density was determined according to the formula: $\Delta OD = \log(10)(\% Tb/\% Ta)$, where % Tb is the percent transmission in the bleached state, % Ta is the percent transmission in the activated state. The $\Delta OD$ at saturation is after 15 minutes of activation and the Fade Half Life ("T½") value is the time interval in seconds for the $\Delta OD$ of the activated form of the photochromic material in the coating to reach one half the fifteen minute $\Delta OD$ at 73.4° F. (23° C.), after removal of the activating light source.

Delta $E_{\%~T}$ and ESF are calculated according to the equations below.

$$\text{Delta } E_{\%~T} = [(\% T - \% T_o)^2 + (a^* - a^*_o)^2 + (b^* - b^*_o)^2]^{0.5} \qquad \text{Equation 1}$$

$$ESF = [(\text{sum of Hammett } \sigma_p \text{ values for } R^3 \text{ and } R^4)) \times 10] + (\text{sum of steric } A \text{ values for } R^1 \text{ and } R^2) \qquad \text{Equation 2}$$

The measured a*, b*, and percent transmission values for the transparent substrate were as follows: $a^*_o$ of −0.07, $b^*_o$ of 0.3, and % $T_0$ of 92.3. These values were determined as reported above.

Table 7 shows the color properties and kinetic data for compounds where $R^3$ and $R^4$ are methoxy, including Examples 1 to 7 and comparative examples CE1 to CE5. Structures for Examples 1 to 7 and CE1 to CE5 can be found in Table 3.

TABLE 7

| Example# | ESF | Delta $E_{\%T}$ | Bleach State %T | a* | b* | Fade $\Delta OD$ | T½ (sec) |
|---|---|---|---|---|---|---|---|
| 1 | 4.6 | 3.23 | 89.8 | −0.6 | 2.3 | 0.47 | 26 |
| 2 | 4.6 | 3.68 | 89.3 | −0.5 | 2.5 | 0.50 | 26 |
| 3 | −0.4 | 6.04 | 86.8 | −0.3 | 2.9 | 0.37 | 18 |
| 4 | −1.2 | 4.75 | 87.8 | 0.3 | 1.8 | 0.26 | 13 |
| 5 | −1.8 | 6.22 | 86.7 | −0.2 | 2.9 | 0.34 | 17 |
| 6 | −2.0 | 6.71 | 86.2 | −0.2 | 3.1 | 0.28 | 13 |
| 7 | −3.3 | 6.27 | 86.5 | 0.1 | 2.4 | 0.22 | 11 |
| CE1 | −4.8 | 9.90 | 82.8 | −0.1 | 2.8 | 0.27 | 13 |
| CE2 | −5.4 | 7.89 | 85.0 | −0.2 | 3.3 | 0.22 | 11 |
| CE3 | −5.4 | 8.95 | 84.0 | −0.1 | 3.5 | 0.30 | 13 |
| CE4 | −5.4 | 11.58 | 83.5 | −2.2 | 7.5 | 0.26 | 12 |
| CE5 | −5.4 | 14.12 | 78.6 | 0.8 | 3.7 | 0.29 | 13 |

The results in Table 7 clearly demonstrate the improved bleach color, indicated by lower Delta E % $O_T$ values, provided by compounds of the present invention as compared to similar compounds with ESF values outside of the scope of the invention. For example, the indolenaphthopyran compounds of the present invention have lower Delta E % $O_T$ values than indolenaphthopyran compounds which lack an $R^1$ or $R^2$ substituent with significant steric bulk to obtain an ESF value of at least −3.3, such as comparative examples CE1 to CE4 and CE5. Desirable Delta $E_{\%~T}$ values are achieved by having desirable percent transmission, a*, and b* values. Comparative example CE5 has a relatively low percent transmission value, 78.6%, and relatively high a* and b* values, which leads to a high Delta $E_{\%~T}$ value of 14.12. In comparison, Example 1 has a higher percent transmission value of 89.8%, and a* and b* values closer to zero, leading to a desirable Delta $E_{\%~T}$ value of 3.23. The indolenaphthopyran compounds of the present invention also exhibit lower Delta $E_{\%~T}$ values than indolenaphthopyran compounds that have alkyl-substitution on the indole nitrogen rather than aryl-substitution on the indole nitrogen, such as CE4. The $\Delta OD$ and Fade $T_2$ values were included in Table 7, and reported hereinafter, to indicate the compounds of the present invention are thermally reversible photochromic compounds.

Table 8 shows the color properties and kinetic data for compounds where $R^3$ is morpholino, including Examples 8 to 12 and comparative examples CE6 to CE8. Structures for Examples 8 to 12 and CE6 to CE8 can be found in Table 3.

TABLE 8

| Example# | Delta ESF | Bleach State E%T | % T | a* | b* | ΔOD | Fade T½ (sec) |
|---|---|---|---|---|---|---|---|
| 8 | 4.1 | 4.21 | 88.6 | −0.3 | 2.2 | 0.70 | 33 |
| 9 | 3.5 | 3.54 | 89.2 | −0.3 | 2.0 | 0.71 | 34 |
| 10 | −1.5 | 5.87 | 86.6 | 0.2 | 1.2 | 0.55 | 24 |
| 11 | −2.3 | 6.31 | 83.6 | 0.7 | 0.0 | 0.46 | 24 |
| 12 | −2.9 | 6.87 | 85.6 | 0.4 | 1.2 | 0.54 | 23 |
| CE6 | −5.0 | 10.67 | 81.7 | 0.6 | −0.8 | 0.23 | 12 |
| CE7 | −6.5 | 8.34 | 84.0 | 0.5 | 0.9 | 0.33 | 13 |
| CE8 | −6.5 | 12.80 | 80.1 | 0.5 | 3.8 | 0.42 | 22 |

The results in Table 8 clearly demonstrate the improved bleach color, indicated by lower Delta $E_{\%T}$ values, provided by compounds of the present invention as compared to similar compounds with ESF values outside of the scope of the invention. Due to the strongly electron donating nature of the morpholino $R^3$ substituent, significant steric bulk of $R^1$ and/or $R^2$ groups is required to achieve the desired ESF value and color properties. For example, the indolenaphthopyran compounds of the present invention have lower Delta $E_{\%T}$ values than indolenaphthopyran compounds which lack an $R^1$ or $R^2$ substituent with significant steric bulk to have an ESF value of at least −3.3, such as comparative examples CE6 and CE7. The indolenaphthopyran compounds of the present invention also exhibit lower Delta $E_{\%T}$ values than indolenaphthopyran compounds that have alkyl-substitution on the indole nitrogen rather than aryl-substitution on the indole nitrogen, such as CE8.

Table 9 shows the color properties and kinetic data for compounds where $R^3$ and $R^4$ are hydrogen, including Examples 13 to 21 and comparative examples CE9 to CE11. Structures for Examples 13 to 21 and CE9 to CE.3 can be found in Table 3.

TABLE 9

| Example# | Delta ESF | Bleach State E%T | % T | a* | b* | ΔOD | Fade T½ (sec) |
|---|---|---|---|---|---|---|---|
| 13 | 10.0 | 2.47 | 91.9 | −1.0 | 2.6 | 0.58 | 108 |
| 14 | 10.0 | 2.16 | 91.9 | −0.9 | 2.4 | 0.57 | 100 |
| 15 | 5.0 | 2.76 | 91.2 | −1.0 | 2.8 | 0.49 | 69 |
| 16 | 4.2 | 1.71 | 91.6 | −0.4 | 1.8 | 0.46 | 65 |
| 17 | 3.6 | 2.77 | 91.2 | −0.9 | 2.7 | 0.47 | 69 |
| 18 | 3.4 | 3.02 | 90.6 | −0.8 | 2.8 | 0.4 | 50 |
| 19 | 2.1 | 1.93 | 91.3 | −0.5 | 2.0 | 0.35 | 40 |
| 20 | 1.2 | 3.02 | 90.7 | −0.8 | 2.7 | 0.40 | 50 |
| 21 | 0.6 | 2.54 | 91.1 | −0.8 | 2.5 | 0.37 | 41 |
| CE9 | 0.0 | 3.47 | 90.0 | −0.8 | 2.9 | 0.34 | 41 |
| CE10 | 0.0 | 3.90 | 89.8 | −1.0 | 3.2 | 0.42 | 51 |
| CE11 | 0.0 | 5.03 | 89.6 | −1.7 | 4.3 | 0.36 | 62 |

The results in Table 9 clearly demonstrate the improved bleach color, indicated by lower Delta $E_{\%T}$ values, provided by compounds of the present invention as compared to similar compounds which lack at least one $R^1$ or $R^2$ group with a steric bulk A of at least 0.6. For example, the indolenaphthopyran compounds of the present invention have lower Delta $E_{\%T}$ values than indolenaphthopyran compounds where $R^1$ and $R^2$ are hydrogen, such as comparative examples CE9 and CE10. The indolenaphthopyran compounds of the present invention also exhibit lower Delta $E_{\%T}$ values than indolenaphthopyran compounds that have alkyl-substitution on the indole nitrogen rather than aryl-substitution on the indole nitrogen, such as CE11.

Table 10 shows the color properties and kinetic data for compounds having $R^5$ and $R^6$ substituents, including Examples 22 to 27 and comparative examples CE12 to CE14. Structures for Examples 22 to 24 and CE 12 can be found in Table 4. Structures for Examples 25 and CE13 can be found in Table 5. Structures for Examples 26 and 27 and CE 14 can be found in Table 6.

TABLE 10

| Example# | Delta ESF | Bleach State E%T | % T | a* | b* | ΔOD | Fade T½ (sec) |
|---|---|---|---|---|---|---|---|
| 22 | 7.3 | 5.5 | 90.9 | −2.3 | 5.2 | 0.69 | 74 |
| 23 | 1.5 | 5.7 | 88.5 | −1.5 | 4.3 | 0.49 | 37 |
| 24 | 2.3 | 6.2 | 89.5 | −2.3 | 5.4 | 0.53 | 48 |
| 25 | 1.5 | 8.7 | 88.8 | −3.3 | 7.6 | 0.45 | 40 |
| 26 | 1.5 | 4.7 | 89.4 | −0.7 | 4.0 | 0.27 | 31 |
| 27 | 2.3 | 6.3 | 89.0 | −1.1 | 5.5 | 0.32 | 41 |
| CE12 | −2.7 | 7.5 | 87.9 | −2.4 | 5.9 | 0.39 | 23 |
| CE13 | −2.7 | 11.8 | 88.0 | −4.4 | 10.4 | 0.35 | 25 |
| CE14 | −2.7 | 7.0 | 88.6 | −1.2 | 6.2 | 0.21 | 19 |

The results in Table 10 clearly demonstrate the improved bleach color, indicated by lower Delta $E_{\%T}$ values, provided by compounds of the present invention as compared to similar compounds which lack at least one $R^1$ or $R^2$ group with a steric bulk A of at least 0.6. For example, the indolenaphthopyran compounds of the present invention have lower Delta $E_{\%T}$ values than indolenaphthopyran compounds where $R^1$ and $R^2$ are hydrogen, such as comparative examples CE12 to CE14.

The present invention can be further characterized by one or more of the following non-limiting clauses.

Clause 1. An indolenaphthopyran compound comprising the core skeletal structure represented by Formula (Ib),

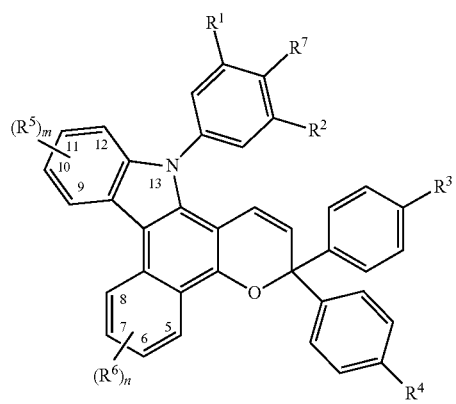

Formula (Ib)

wherein,
$R^1$ and $R^2$ each independently have a steric bulk A,
wherein at least one of $R^1$ or $R^2$ has a steric bulk A of at least 0.6,
$R^3$ and $R^4$ each independently have a Hammett $\sigma_p$ value,
wherein the indolenaphthopyran compound has a calculated electronic steric factor of at least −3.3;
m is 0 to 4;
n is 0 to 4; and
$R_5$, $R^6$, and $R^7$ are each independently hydrogen or a group other than hydrogen.

Clause 2. The indolenaphthopyran compound of clause 1, wherein the indolenaphthopyran compound has a calculated electronic steric factor of at least 0.

Clause 3. The indolenaphthopyran compound of clauses 1 or 2, wherein at least one of $R^1$ and $R^2$ are each independently alkyl, alkoxy, haloalkyl, or a nitrogen-containing heterocycle.

Clause 4. The indolenaphthopyran compound of any of clauses 1 to 3, wherein at least one of $R^3$ and $R^4$ are each independently hydrogen, alkyl, alkoxy, haloalkyl, or a nitrogen-containing heterocycle.

Clause 5. The indolenaphthopyran compound of any of clauses 1 to 4, wherein at least one of $R^1$ or $R^2$ is methyl, ethyl, butyl, tert-butyl, trifluoromethyl, or methoxy.

Clause 6. The indolenaphthopyran compound of any of clauses 1 to 5, wherein both $R^1$ and $R^2$ are the same group.

Clause 7. The indolenaphthopyran compound of any of clauses 1 to 6, wherein at least one of $R^3$ or $R^4$ is methoxy or trifluoromethyl.

Clause 8. The indolenaphthopyran compound of any of clauses 1 to 7,
wherein,
m is 0 to 4, n is 0 to 4; and
$R^5$ independently for each m and $R^6$ independently for each n are
i. hydroxyl;
ii. cyano;
iii. (meth)acrylate;
iv. amino or nitrogen-containing heterocycle;
v. a mesogen-containing group L;
vi. substituted or unsubstituted alkyl;
vii. substituted or unsubstituted alkenyl;
viii. substituted or unsubstituted alkynyl;
ix. a halo group;
x. a perhalo group;
xi. boronic ester or boronic acid;
xii. polyether, polyester, polycarbonate, or polyurethane;
xiii. substituted or unsubstituted aryl;
xiv. substituted or unsubstituted heterocycloalkyl;
xv. substituted or unsubstituted heteroaryl;
xvi. substituted or unsubstituted alkoxy or substituted or unsubstituted aryloxy;
xvii. substituted or unsubstituted alkylthio or substituted or unsubstituted arylthio;
xviii. ketone, aldehyde, ester, carboxylic acid, carboxylate, or amide;
xix. carbonate, carbamate, or urea; or
xx. siloxane, alkoxysilane, or polysiloxane.

Clause 9. The indolenaphthopyran of clause 8, wherein each alkyl substituent, each alkenyl substituent, each alkynyl substituent, each aryl substituent, each heterocycloalkyl substituent, each heteroaryl substituent, each alkoxy substituent, each aryloxy substituent, each alkylthio substituent, and each arylthio substituent is in each case independently selected from halogen, cyano, nitro, alkyl, alkenyl, alkynyl, haloalkyl, perhaloalkyl, heterocycloalkyl, aryl, heteroaryl, alkoxy, hydroxyl, alkylthio, ketone, aldehyde, ester, carboxylic acid, carboxylate, siloxane, alkoxysilane, polysiloxane, amide, amine, carbamate, carbonate, urea, polyester group, polyether group, polycarbonate group, polyurethane group, an acrylate group, a methacrylate group, aryl amine, alkyl amine, cyclic aminos, heteroaromatics, or combinations thereof.

Clause 10. The indolenaphthopyran of clauses 8 or 9, wherein each mesogen-containing group $L^1$ is independently represented by the following Formula (II),

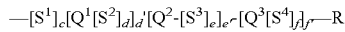   Formula (II)

wherein,
(a) $Q^1$, $Q^2$, and $Q^3$ for each occurrence, are independently a divalent group selected from the group consisting of unsubstituted aryl, substituted aryl, unsubstituted cycloalkyl, and substituted cycloalkyl;
wherein the aryl substituents and cycloalkyl substituents are each independently selected from the group consisting of liquid crystal mesogens, halogen, alkyl, alkoxy, alkylamino, dialkylamino, alkylthio, alkoxycarbonyl, alkylcarbonyl, alkoxycarbonyloxy, aryloxycarbonyloxy, perfluoroalkyl, and perfluoroalkoxy;
(b) c, d, e, and f are each independently an integer of 0 to 3; and each $S^1$, $S^2$, $S^3$, and $S^4$ is independently chosen for each occurrence from a spacer unit selected from the group consisting of:
(i.) —C(Z)$_2$—, —N(Z)—, —C(Z)=C(Z)—, —C(Z)=N—, wherein Z for each occurrence is independently selected from the group consisting of hydrogen, alkyl, or aryl;
(ii) —Si(CH$_3$)$_2$—, —Si(CH$_3$)$_2$O—; and
(iii) —O—, —C(=O)—, —C≡C—, —N=N—, —S—, —S(=O)—, —(O=)S(=O)—, —(O=)S(=O)O—, —O(O=)S(=O)O—
provided that when two spacer units comprising heteroatoms are linked together the spacer units are linked so that heteroatoms are not directly linked to each other;
(c) R is alkyl; and
(d) d', e' and f' are each independently 0, 1, 2, 3, and 4, provided that the sum of d'+e'+f' is at least 1.

Clause 11. The indolenaphthopyran compound of any of clauses 8 to 10, wherein $R^7$ is selected from the group consisting of alkyl, alkoxy, haloalkyl, and a nitrogen-containing heterocycle.

Clause 12. The indolenaphthopyran compound of clause 1, wherein $R^1$ is trifluoromethyl, $R^2$ is trifluoromethyl or hydrogen, $R^3$ is hydrogen, and $R^4$ is hydrogen.

Clause 13. The indolenaphthopyran compound of any of clauses 1 to 12, wherein the formula comprises at least one additional substituent, identical or different, located on at least one available position on the core skeletal structure among positions 5, 6, 7, 8, 9, 10, 11, or 12 depicted therein.

Clause 14. The indolenaphthopyran compound of clause 13, wherein said at least one additional substituent is independently selected from alkyl group, heterocycloalkyl group, aryl group, heteroaryl group, thiol groups, alkylthio groups, arylthio groups, ketone groups, aldehyde groups, ester groups, carboxylic acid groups, phosphoric acid groups, phosphoric acid ester groups, sulfonic acid groups, sulfonic acid ester groups, nitro groups, cyano groups, alkyl groups, aralkyl groups, alkenyl groups, alkynyl groups, haloalkyl groups, perhaloalkyl groups, heterocycloalkyl groups, aryl groups, alkaryl groups, hydroxyl substituted aryl groups, alkoxy substituted aryl groups, heterocycloalkyl substituted aryl groups, halo substituted aryl groups, polyfused-ring aryl groups, heteroaryl groups, poly-fused-ring heteroaryl groups, amine groups, carboxylate groups, siloxane groups, alkoxysilane groups, polysiloxane groups, amide groups, carbamate groups, carbonate groups, urea groups, polyester groups, polyether groups, polycarbonate groups, polyurethane groups, acrylate groups, methacrylate groups, aryl amino groups, cyclic amino groups, heteroaromatic groups, or combinations thereof.

Clause 15. A photochromic composition comprising the indolenaphthopyran compound of any of clauses 1 to 14.

Clause 16. A photochromic article comprising the indolenaphthopyran compound of any of clauses 1 to 14, wherein the photochromic article is selected from the group consisting of ophthalmic articles, display articles, windows, mirrors, active liquid crystal cell articles, and passive liquid crystal cell articles; or wherein the photochromic article is an ophthalmic article selected from the group consisting of corrective lenses, non-corrective lenses, contact lenses, intra-ocular lenses, magnifying lenses, protective lenses, and visors; or wherein the photochromic article is a display article selected from the group consisting of screens, monitors, and security elements.

Clause 17. The use of an indolenaphthopyran compound of any of clauses 1 to 14 to prepare a photochromic article.

The present invention has been described with reference to specific details of particular embodiments thereof. It is not intended that such details be regarded as limitations upon the scope of the invention except insofar as to the extent that they are included in the accompanying claims.

What is claimed is:

1. An indolenaphthopyran compound represented by Formula (I),

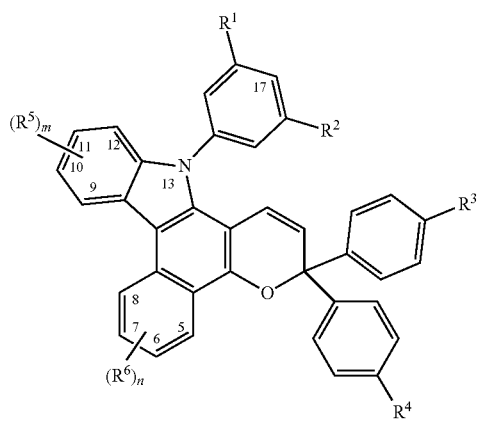

Formula (Ia)

wherein,
$R^1$ and $R^2$ each independently have a steric A value, wherein at least one of $R^1$ or $R^2$ has a steric A value of at least 0.6, and at least one of $R^1$ and $R^2$ is, in each case independently, alkyl, alkoxy, or perfluoroalkyl,
$R^3$ and $R^4$ each independently have a Hammett σp value, wherein at least one of $R^3$ and $R^4$ is, in each case independently, hydrogen, alkyl, acyclic alkyl amine, alkoxy, fluoro, or a nitrogen-containing heterocycle selected from morpholino, piperidino, and pyrrolidino,
wherein the indolenaphthopyran compound has a calculated electronic steric factor of at least −3.3, wherein the electronic steric factor (ESF) is calculated in accordance with the following equation, ESF=[(sum of Hammett $\sigma_p$ values for $R^3$ and $R^4$))× 10]+(sum of steric $A$ values for $R^1$ and $R^2$)

m is 0 to 4, n is 0 to 4; and
$R^5$ independently for each m and $R^6$ independently for each n are:
alkyl;
a perfluoroalkyl group; or
alkoxy.

2. The indolenaphthopyran compound of claim 1, wherein the indolenaphthopyran compound has a calculated electronic steric factor of at least 0.

3. The indolenaphthopyran compound of claim 1, wherein at least one of $R^1$ or $R^2$ is methyl, ethyl, butyl, tert-butyl, trifluoromethyl, or methoxy.

4. The indolenaphthopyran compound of claim 1, wherein both $R^1$ and $R^2$ are the same group.

5. The indolenaphthopyran compound of claim 1, wherein at least one of $R^3$ or $R^4$ is methoxy, fluoro, or morpholino.

6. The indolenaphthopyran compound of claim 1, represented by Formula (Ib):

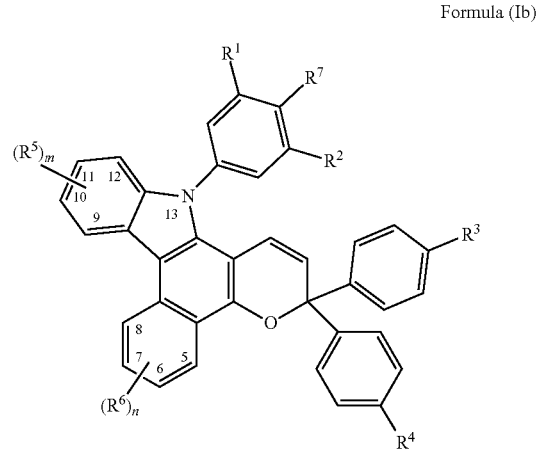

Formula (Ib)

wherein $R^7$ is selected from the group consisting of alkyl, alkoxy, haloalkyl, and a nitrogen-containing heterocycle selected from morpholino, piperidino, and pyrrolidino.

7. The indolenaphthopyran compound of claim 1, wherein $R^1$ is trifluoromethyl, $R^2$ is trifluoromethyl or hydrogen, $R^3$ is hydrogen, and $R^4$ is hydrogen.

8. A photochromic composition comprising the indolenaphthopyran compound of claim 1.

9. A photochromic article comprising the indolenaphthopyran compound of claim 1, wherein the photochromic article is selected from ophthalmic articles, display articles, windows, mirrors, active liquid crystal cell articles, or passive liquid crystal cell articles.

10. The photochromic article of claim 9, wherein the photochromic article is selected from ophthalmic articles, and the ophthalmic articles are selected from corrective lenses, non-corrective lenses, contact lenses, intra-ocular lenses, magnifying lenses, protective lenses, or visors.

11. The photochromic article of claim 9, wherein the photochromic article is selected from display articles, and the display articles are selected from screens, monitors, or security elements.

* * * * *

UNITED STATES PATENT AND TRADEMARK OFFICE
CERTIFICATE OF CORRECTION

PATENT NO. : 12,344,617 B2  
APPLICATION NO. : 17/416058  
DATED : July 1, 2025  
INVENTOR(S) : Ryan Stayshich et al.

Page 1 of 1

It is certified that error appears in the above-identified patent and that said Letters Patent is hereby corrected as shown below:

On the Title Page

Column 1, item (54) Title, Line 1, delete "Indolonaphthopyrans" and insert -- Indolenaphthopyran --

Column 2, item (57) Abstract, Line 5, delete "σp" and insert -- $\sigma_p$ --

In the Specification

Column 1, Line 1, delete "Indolonaphthopyrans" and insert -- Indolenaphthopyran --

In the Claims

Column 57, Line 19, Claim 1, delete "(I)," and insert -- (Ia), --

Column 57, Line 46, Claim 1, delete "6p" and insert -- $\sigma_p$ --

Signed and Sealed this  
Ninth Day of September, 2025

Coke Morgan Stewart  
*Acting Director of the United States Patent and Trademark Office*